(12) United States Patent
Viseux et al.

(10) Patent No.: US 9,260,460 B2
(45) Date of Patent: Feb. 16, 2016

(54) ORGANOGOLD COMPLEXES AND METHODS FOR MAKING THE SAME

(75) Inventors: Eddy Michel Elie Viseux, Brighton (GB); Christopher Gallop, Brighton (GB); Mariusz Bobin, Brighton (GB)

(73) Assignee: The University of Sussex, Brighton Sussex (GB)

( * ) Notice: Subject to any disclaimer, the term of this patent is extended or adjusted under 35 U.S.C. 154(b) by 0 days.

(21) Appl. No.: 14/008,618

(22) PCT Filed: Mar. 30, 2012

(86) PCT No.: PCT/GB2012/000301
§ 371 (c)(1),
(2), (4) Date: Sep. 30, 2013

(87) PCT Pub. No.: WO2012/131313
PCT Pub. Date: Oct. 4, 2012

(65) Prior Publication Data
US 2014/0039200 A1 Feb. 6, 2014

(30) Foreign Application Priority Data

Mar. 31, 2011 (GB) .................................. 1105511.8
Mar. 31, 2011 (GB) .................................. 1105531.6

(51) Int. Cl.
| | | |
|---|---|---|
| C07F 1/12 | (2006.01) | |
| C07F 9/572 | (2006.01) | |
| C07B 53/00 | (2006.01) | |
| C07C 271/20 | (2006.01) | |
| C07C 271/22 | (2006.01) | |
| C07C 311/51 | (2006.01) | |
| C07D 209/20 | (2006.01) | |
| C07F 9/50 | (2006.01) | |

(52) U.S. Cl.
CPC .............. *C07F 9/5728* (2013.01); *C07B 53/00* (2013.01); *C07C 271/20* (2013.01); *C07C 271/22* (2013.01); *C07C 311/51* (2013.01); *C07D 209/20* (2013.01); *C07F 1/12* (2013.01); *C07F 9/5045* (2013.01); *C07F 9/5721* (2013.01)

(58) Field of Classification Search
CPC ......................................................... C07F 1/12
USPC ......................................................... 556/110
See application file for complete search history.

(56) References Cited

U.S. PATENT DOCUMENTS 5,288,912 A 2/1994 Devon
2011/0021806 A1 1/2011 Zhang et al.

FOREIGN PATENT DOCUMENTS

| FR | 2853652 | 10/2004 |
|---|---|---|
| WO | 2006002470 | 1/2006 |
| WO | 2006119283 | 11/2006 |
| WO | 2012131313 | 10/2012 |

OTHER PUBLICATIONS

Brooks, Peter et al., "Organophosphorus Intermediates, IX* The Cleavage of a, -bisdiphenylphosphinoalkanes with Lithium. A 31 P N.M.R. Study", Australian Journal of Chemistry 40 (1987) pp. 1341-1351.
Cereghetti, Marco et al., "(R)- and (S)-6,6'-Dimethyl- and 6,6'-Dimethoxy-2,2'- diiodo-1,1'-biphenyls: Versatile Intermediates for the Synthesis of Atropisomeric Diphosphine Ligands", Tetrahedron Letters vol. 37, No. 30 (1996) pp. 5347-5350.
Chen, Zili et al., "Gold catalyzed diastereoselective cascade allylation/enyne cycloisomerization to construct densely functionalized oxygen hetereocycles", Organic Letters vol. 12, No. 15 (2010) pp. 3468-3471.
Hamada, Takayuki et al., "P-chirogenic binaphthyl-substituted monophosphines: synthesis and use in enolate vinylation/arylation reactions", Organic Letters vol. 4, No. 6 (2002) pp. 999-1001.
"International Search Report and Written Opinion", for International Application No. PCT/GB2012/000301, dated Jul. 20, 2012, 35 pages.
Kerrigan, Nessan J. et al., "Studies in the preparation of novel P-chirogenic binaphthyl monophosphanes (MOPs)", Tetrahedron Letters 44 (2003) pp. 8461-8465.
Koleva, B. B. et al., "Mononuclear Au(III)-complexes with tryptophan-containing dipeptides: Sythesis, spectroscopic and structural elucidation", Inorganic Chimica Acta 360 (2007) pp. 2224-2230.
Marshall, Daniel R. et al., "a-Methyltryptamine sulfonamide derivatives as novel glucocorticoid receptor ligands", Bioorganic & Medicinal Chemistry Letters 17 (2007) pp. 315-319.
Mason, Lucas J. et al., "Lithium bis(2-phenylphosphidoethyl)phenyl-phosphine: a reactive phosphorus intermediate", Heteroatom Chemistry vol. 18, No. 6 (2007) pp. 675-678.
Mezailles, Nicolas et al., "Phosphine gold(I) bis-(trifluoromethanesulfonyl)imidate complexes as new highly efficient and air-stable catalysts for the cycloisomerization of enynes", Organic Letters vol. 7, No. 19 (2005) pp. 4133-4136.
Miller, Jeremie J. et al., "Synthesis of amine functionalized oxazolines with applicatoins in asymmetric catalysis", Tetrahedron 65 (2009) pp. 3110-3119.
Nagel, Ulrich et al., "Neue liganden mit vier stereozentren. Synthese und trennung der drei diastereomeren [P(R,S),3R,4R,P'(R,S)]-3,4-bis(methylphenylphosphino)-pyrrolidine", Chemische Berichte 121 (1988) pp. 1123-1131.
Hamilton, Gregory L. et al., "A Powerful Chiral Counterion Strategy for Asymmetric Transition Metal Catalysis", Science 317, 496 (2007); DOI: 10.1126/science.1145229.
Munoz, M. P. et al., "Ligand Effects in Gold- and Platinum-Catalyzed Cyclization of Enynes: Chiral Gold Complexes for Enantioselective Alkoxycyclization", Organometallics 2005, 24, 1293-1300.

(Continued)

*Primary Examiner* — Shawquia Jackson
(74) *Attorney, Agent, or Firm* — Pauly, Devries Smith & Deffner, LLC

(57) ABSTRACT

The present invention relates to chiral ligands deriving from α- and β-amino acids, and from metal complexes formed from the same. The ligands are useful with catalytic gold complexes, particularly Au(I) complexes.

18 Claims, No Drawings

(56) References Cited

OTHER PUBLICATIONS

Hashmi, A. Stephen "Homogeneous Catalysis by Gold," Gold Bulleton 2004, 37/1-2 (15 pages).

Koch, Daniela et al., "Phosphine Gold(I), Nickel(II) and Platinum(II) Complexes with the Anion of Hydantoin and of 3,4 Pyridine Dicarboxylic Imide," Metal Complexes of Biologically Important Ligands, CXI [1], 1998 (7 pages).

Liu, Shiuh-Tzung et al., "N-Heterocyclic Carbene Transfer from Gold(I) to Palladium(II)," Organometallics, 2009 (6 pages)

"Reactions of (tertiary phosphine)gold(I) substituted imidazoles or pyrazolones with acidic reagents: protonation, azole displacement, and adduct formation. Crystal structure determination of the adduct 1-methyl-2 (cyclohexylphosphinegoldthiolato) imidazole," Journal of Organometallic Chemistry, 344 (1988) 119-135 (17 pages)

Rudolph, M et al., "Gold Complexes for the Synthesis of Dihydrobenzofurans, Dihydrochromenes and Dihydroindoles," 22th. International Conference on Organometallic Chemistry ICOMC 2006), Book of Abstracts, Poster Presentations, Zaragoza, Spain,, vol. 2, Jul. 23, 2006, p. P513 (1 page).

ORGANOGOLD COMPLEXES AND METHODS FOR MAKING THE SAME

The present invention relates to new chiral ligands for gold, gold complexes of these ligands, and the use thereof in catalytic reactions. In particular, the gold complexes of the present invention are useful in stereoselective carbon-carbon bond-forming reactions.

BACKGROUND OF THE INVENTION

Generally there are three different sources of gold(I) that can be used to catalyse a reaction. One source is gold(III) salts that are reduced in situ to gold(I) to catalyse a reaction. In such systems, it is not always clear to see whether gold(I) or gold(III) is the active species. Another source of gold(I) is the use of a simple inorganic gold(I) salt such as AuCl. Finally gold(I) can be used as a phosphine-stabilised cationic gold species, eg $[Ph_3PAu]^+$, with coordinating anions such as $[TfO]^-$, $[SbF_6]^-$, $[PF_6]^-$. These species are generally formed in situ with the assistance of a silver salt containing the appropriate anion. This method of using a silver co-catalyst in the presence of a gold(I)phosphine is generally the method of choice seen in most gold(I) catalysed transformations.

Despite the use of a gold(I) phosphine and a silver salt as a co-catalyst being the most common catalytic system in gold (I) catalysis, there are some problems inherent in this methodology. Silver salts are known to be hygroscopic and light sensitive which can be an issue when weighing out the reagent, especially in small quantities. In 2005 Gagosz at al. documented some other possible drawbacks of using silver salts and suggest that the resultant phosphine gold(I) complexes may be unstable in solution (*Org. Lett.*, 2005, 7, 4133-4136). Gagosz at al. developed a new phosphine gold(I) catalyst $Ph_3PAuNTf_2$ (*Org. Lett.*, 2005, 7, 4133-4136), which was found to be air stable and easy to handle.

The first example of an asymmetric gold catalysed transformation, an aldol reaction between isocyanoacetates and aldehydes, was reported by Hayashi et al. in 1986 (*J. Am. Chem. Soc.*, 1986, 108, 6405-6406). In general, most gold-based asymmetric catalysts use a chiral phosphine ligand to induce enantioselectivity in a transformation. In 2007 Toste et al. demonstrated that this approach is not always successful and reported that a chiral counterion could be used for an asymmetric hydroalkoxylation of allenols (*Science*, 2007, 317, 496-499). This example of chiral induction by a chiral ion pair shows that the chiral auxiliary does not necessarily need to be in the first coordination sphere of the gold(I) centre. The chiral ion pair can produce good enantioselectivity where traditional chiral ligands cannot. The combination of both strategies has also resulted in superior enantiomeric excesses compared to the use of only one of the two strategies.

There remains a need for further chiral ligands for gold and gold complexes containing the same that are active as asymmetric catalysts.

SUMMARY OF THE INVENTION

In one aspect, the present invention provides an enantiomerically enriched compound of formula (I)

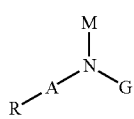

(I)

wherein

M denotes a group which allows transfer of the nitrogen to a gold atom, such as hydrogen, an alkali metal or $SiR^{14}_3$ wherein each $R^{14}$ is independently $C_1$-$C_4$ alkyl or phenyl;

A denotes $SO_2$, $C(=O)$, or $P(O)(R^1)_2$;

each $R^1$ independently denotes alkyl or cycloalkyl; or optionally substituted aryl;

R denotes hydrogen, alkyl or haloalkyl; or optionally substituted (hetero)aryl; and G denotes a group deriving from an α- or β-amino acid.

The term "enantiomerically enriched compound" means that one of the enantionmers of the compound is present in excess compared to the other enantiomer. This excess will hereinafter be referred to as "enantiomeric excess" or "e.e.". Enantiomeric excess can be determined, for example, by chiral GLC or HPLC analysis. The enantiomeric excess is equal to the difference between the amount of enantionmers divided by the sum of the amount of the enantiomers, which quotient can be expressed as a percentage after multiplication by 100. The term "enantiomerically enriched" encompasses both pure stereoisomers (i.e. only one enantiomer being present) and mixtures of two enantiomers.

Preferably, the term "enantiomerically enriched" means that the enantiomeric excess is at least 90%, more preferably at least 95%, more preferably at least 99%, more preferably at least 99.9%. Most preferably, the term "enantiomerically enriched" means that the compound consists of only one of the enantiomers (i.e. the enantiomeric excess is 100%).

The M substituent in the compound of formula (I) can be replaced with a catalytic metal centre, such as Au(I). As such, the present invention further relates to an enantiomerically enriched compound of formula (II)

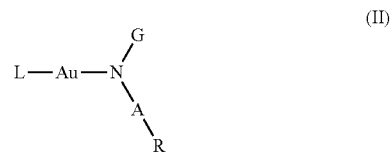

(II)

wherein

L denotes a phopshine, thioether, amine or N-heterocyclic carbene ligand;

A denotes $SO_2$, $C(=O)$, or $P(O)(R^1)_2$;

each $R^1$ independently denotes alkyl or cycloalkyl; or optionally substituted aryl;

R denotes hydrogen, alkyl, or haloalkyl; or optionally substituted (hetero)aryl; and G denotes a group deriving from an α- or β-amino acid, wherein optionally together G and L may combine to form a macrocycle containing the Au metal, or alternatively L may derive from a G substituent in an identical compound of formula (II), such that a macrocycle containing two Au atoms is formed, with the L substituent on each Au metal atom deriving from the G substituent on the corresponding compound of formula (II).

The G substituent in the compound of formula (II) may contain a moiety that is capable of coordinating to a metal centre. In such embodiments, this moiety in the G substituent may combine with the L substituent in the compound of formula (II) to form a macrocycle containing the Au metal. As such, the present invention further relates to an enantiomerically enriched compound of formula (III)

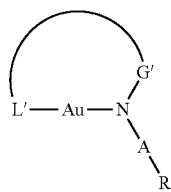

(III)

wherein

A denotes SO$_2$, C(=O), or P(O)(R$^1$)$_2$;

each R$^1$ independently denotes alkyl or cycloalkyl; or optionally substituted aryl;

R denotes hydrogen, alkyl or haloalkyl; or optionally substituted (hetero)aryl; and together L' and G' denote a group deriving from an α- or β-amino acid, where the L' bonds to the Au atom via a phosphorus, sulphur, nitrogen or N-heterocyclic carbene carbon atom.

The invention further relates to methods of forming compounds of formulae (I) to (III), and to reactions using these compounds. In particular, the compounds of formulae (II) and (III) are active as catalysts in a number of reactions. Thus, the present invention further relates to the use of a compound of formula (II) or formula (III) as a catalyst, and to catalytic reactions using a compound of formula (II) or formula (III).

DESCRIPTION OF THE INVENTION

In the present specification, carbon atoms marked with a "*" are chiral and enantiomerically enriched. Other chiral carbon atoms may of course be present in the compounds of the invention. In the nomenclature of the formula used herein, compounds denoted with ' and " are epimers. In other words, whereas a compound of formula X' may derive from an L-amino acid, a compound of formula X" derives from the corresponding D-amino acid. In general, any reference to a compound of formula X should be interpreted as a reference to a compound of formula X' or X". Thus, a reference to the compound of formula (Ib) should be interpreted as a reference to compounds of formulae (Ib') and (Ib").

The compound of formula (I) contains at least one chiral centre, which is present in the G group. The M substituent in the compounds of formula (I) can be replaced with a catalytic metal centre, such as Au(I) as in the compounds of formulae (II) and (III). The compounds of formula (II) and (III) are active as catalysts in a number of reactions, in particular carbon-carbon bond forming reactions. As such, it is preferable that the compound of formula (I) does not contain any highly nucleophilic substituents (other than the nitrogen bonded to M) or unsaturated carbon-carbon bonds other than aromatic groups. This avoids any unwanted internal reactions or side reactions when complexed to a catalytic metal centre, such as in the compounds of formulae (II) and (III). Preferably, the chiral group X does not contain any groups selected from unprotected carboxylic acid or non-aromatic unsaturated groups. Preferably, the compounds of formula (II) an (Ill) do not contain any acidic protons.

The catalysts generally perform better if they are more soluble in the reaction medium. The particular substituents can therefore be modified to adjust the solubility of the compounds depending on the solvent used to carry out the catalytic reaction. For example, aliphatic chains can be used if the reaction is to be carried out in low polarity solvents, whilst polar groups bearing free nitrogen-based functional groups, amides or carboxylates may be used in higher polarity solvents like acetonitrile or methanol.

By "a group deriving from an α- or β-amino acid" is meant a moiety which contains a chiral α- or β-amino acid which is bonded to the rest of the molecule via its C- or N-terminus. The amino acid can be bonded directly to the N(M)AR moiety via its C-terminus. Alternatively, the N atom itself in N(M)AR can correspond to the N-terminus of the chiral α- or β-amino acid. The invention also allows for a linker group to be included between the N(M)AR moiety and the C- or N-terminus of the chiral α- or β-amino acid, such as a group deriving from a C$_3$-C$_6$-dicarboxylic acid. Further aspects of the invention relate to compounds which contain amino acid derivatives in which the carboxylic acid group of the C-terminus has been replaced with a phosphine group such as PPh$_2$. This phosphine group can form part of a bidentate phosphine ligand such as BINAP, QUINAP, PINAP, PHOX, PINPHOS or the like.

The M moiety allows transfer of the remainder of the compound of formula (I) to a catalytic metal atom, such as Au(I). Various ways of transferring ligands to Au(I) are known in the art, and suitable transfer groups would be known to the skilled person. Such groups include, but are not limited to, hydrogen, an alkali metal or SiR$^{14}_3$ wherein R$^{14}$ is C$_1$-C$_4$ alkyl or phenyl, preferably hydrogen or an alkali metal such as sodium or potassium.

In preferred embodiments, the present invention relates to an enantionmerically enriched compound of formula (Ia)

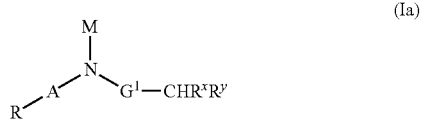

(Ia)

wherein

M denotes hydrogen, an alkali metal or SiR$^{14}_3$ wherein each R$^{14}$ independently denotes C$_1$-C$_4$ alkyl or phenyl;

A denotes SO$_2$, C(=O), or P(O)(R$^1$)$_2$;

R$^1$ denotes C$_1$-C$_4$-alkyl, cyclohexyl or adamantyl; or phenyl optionally substituted with 1 to 5 R$^a$;

R denotes hydrogen, C$_1$-C$_6$-alkyl or C$_1$-C$_6$-fluoroalkyl; phenyl optionally substituted with 1 to 5 R$^a$; or a pyridinyl which is optionally quaternized with hydrogen or methyl;

G$^1$ denotes a bond, —C(=O)(CH$_2$)$_u$— or —C(=O)—(CH$_2$)$_t$-G$^2$;

G$^2$ denotes (C(=O))$_v$NR$^9$; or

G$^2$ and CHR$^x$R$^y$ together denote

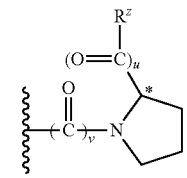

t denotes an integer from 1 to 4;

u denotes 0 or 1;

v denotes 0 or 1;

R$^x$ denotes methyl, ethyl, isopropyl, sec-butyl, 2-methylpropyl, CH(OR$^5$)CH$_3$, (CH$_2$)$_4$OR$^5$, CH$_2$SR$^6$, CH$_2$CH$_2$SCH$_3$, (CH$_2$)$_4$NR$^7$R$^8$, (CH$_2$)$_3$NHC(NH)(NH$_2$), CH$_2$CO$_2$R$^c$, CH$_2$CH$_2$CO$_2$R$^c$, CH$_2$CONR$^9$R$^{10}$, CH$_2$CH$_2$CONR$^9$R$^{10}$,

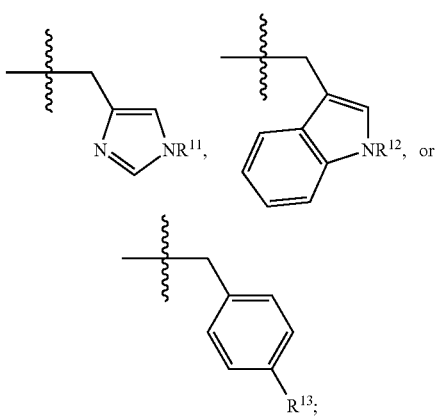

$R^y$ denotes $(CH_2)_u CO_2 R^c$ when $G^1$ denotes a bond;
$R^y$ denotes $(CH_2)_u CO_2 R^c$ or $CH_2 P(R^{15})_2$ when $G^1$ and $G^2$ together denote $—C(=O)(CH_2)_t(C(=O))_v NR^9$;
$R^y$ denotes $N(R^b)_2$ when $G^1$ denotes $—C(=O)(CH_2)_u—$;
$R^z$ denotes $CO_2 R^c$ or $CH_2 P(R^{15})_2$;
each $R^a$ independently denotes halogen, OH, $NO_2$, $C_1$-$C_4$-alkoxy or $N(R^b)_2$;
each $R^b$ independently denotes hydrogen, $C_1$-$C_4$-alkyl, $(CH_2)_{1-4} CO_2 R^c$ or $PG^{am}$;
each $R^c$ independently denotes $C_1$-$C_4$-alkyl, or $PG^{ac}$;
$R^9$ denotes hydrogen or $C_1$-$C_4$-alkyl;
$R^5$ denotes H, $C_1$-$C_4$-alkyl or $PG^{al}$;
$R^6$ denotes H or $R^2$;
$R^2$ denotes $C_1$-$C_4$-alkyl or cyclohexyl;
$R^7$ and $R^8$ independently denote $R^b$ or $R^3$;
$R^3$ denotes $C_1$-$C_4$-alkyl or cyclohexyl;
$R^9$ and $R^{10}$ independently denote H or $C_1$-$C_4$-alkyl;
$R^{11}$ denotes H, $C_1$-$C_4$-alkyl or $C_1$-$C_4$-alkylene-$P(R^1)_2$;
$R^{12}$ denotes H, $C_1$-$C_4$-alkyl or $C_1$-$C_4$-alkylene-$P(R^1)_2$;
$R^{13}$ denotes H, OH or $C_1$-$C_4$-alkoxy;
$R^{15}$ both denote $R^1$ or alternatively one $R^{15}$ denotes phenyl optionally substituted with 1-5 $R^a$ and the other $R^{15}$ denotes 2-naphthyl linked via a carbon-carbon bond at the 1-position to the equivalent position in an $R^{15}$ in another identical compound of formula (Ia) to give $(Ia)_2$;
$PG^{ac}$ denotes a protecting group for a carboxylic acid;
$PG^{am}$ denotes a protecting group for an amine; and
$PG^{al}$ denotes a protecting group for an alcohol.

The M substituent in the compound of formula (Ia) can be replaced with a catalytic metal centre, such as Au(I). The present invention therefore also relates to an enantionamerically enriched compound of formula (IIa)

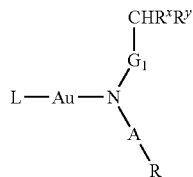

(IIa)

wherein
L denotes $P(R^1)_3$, $S(R^2)_2$, $N(R^3)_3$ or

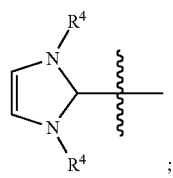

each $R^4$ independently denotes $C_1$-$C_4$-alkyl, cyclohexyl or adamantyl; or phenyl optionally substituted with 1 to 5 $R^a$; and R, $R^1$, $R^2$, $R^3$, A, $G^1$, $R^x$ and $R^y$ are as defined for the compound of formula (Ia).

The compounds of the present invention can be formed by functionalising the C-terminus of an α- or β-amino acid. Thus, the present invention preferably relates to a compound of formula (Ib') or (Ib")

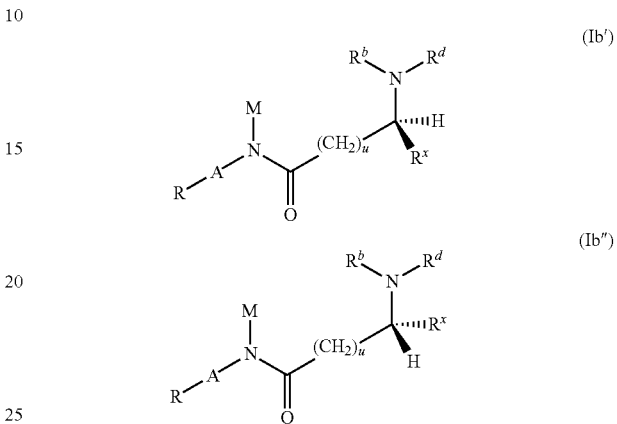

wherein
$R^x$ denotes methyl, ethyl, isopropyl, sec-butyl, 2-methylpropyl, $CH(OR^5)CH_3$, $(CH_2)_4 OR^5$, $CH_2 SR^6$, $CH_2 CH_2 SCH_3$, $(CH_2)_4 NR^7 R^8$, $(CH_2)_3 NHC(NH)(NH_2)$, $CH_2 CO_2 R^c$, $CH_2 CH_2 CO_2 R^c$, $CH_2 CONR^9 R^{10}$, $CH_2 CH_2 CONR^9 R^{10}$,

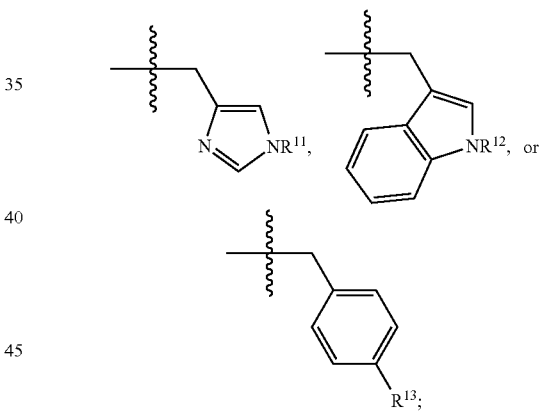

$R^d$ denotes $R^b$; or
$R^d$ and $R^x$ may together form $—(CH_2)_3—$;
u denotes 0 or 1; and
M, A, R, $R^5$, $R^6$, $R^7$, $R^8$, $R^9$, $R^{10}$, $R^{11}$, $R^{12}$, $R^{13}$, $R^b$, and $R^c$ are as defined for the compound of formula (Ia).

The M substituent in the compound of formula (Ib) can be replaced with a catalytic metal centre, such as Au(I). The present invention therefore also relates to a compound of formula (IIb') or (IIb")

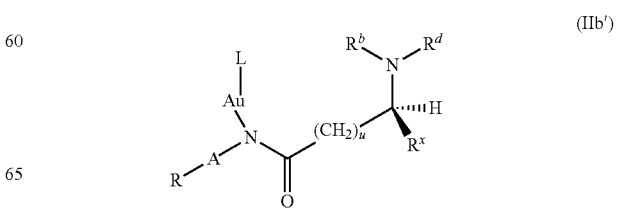

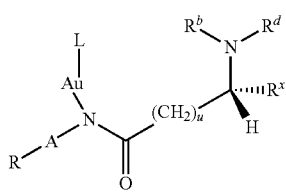

(IIb'')

wherein

L denotes $P(R^1)_3$, $S(R^2)_2$, $N(R^3)_3$ or

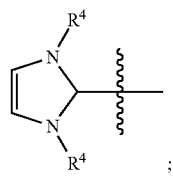

$R^1$ denotes $C_1$-$C_4$-alkyl, cyclohexyl or adamantyl; or phenyl optionally substituted with 1 to 5 $R^a$;

each $R^a$ independently denotes halogen, OH, $NO_2$, $C_1$-$C_4$-alkyl, $C_1$-$C_4$-alkoxy or $N(R^b)_2$;

each $R^2$ independently denotes $C_1$-$C_4$-alkyl or cyclohexyl;

each $R^3$ independently denotes $C_1$-$C_4$-alkyl or cyclohexyl;

each $R^4$ independently denotes $C_1$-$C_4$-alkyl, cyclohexyl or adamantyl; or phenyl optionally substituted with 1 to 5 $R^a$; and A, R, $R^b$, $R^d$, $R^x$ and u are as defined for the compound of formula (Ib).

The compounds of the present invention can also be formed by including a linker group between the N-terminus of an α- or β-amino acid and the coordinating nitrogen atom. Thus, the present invention preferably relates to a compound of formula (Ic') or (Ic'')

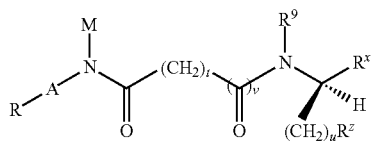

(Ic')

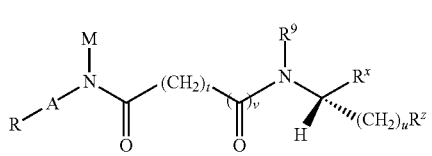

(Ic'')

wherein $R^9$ denotes $R^b$;

$R^x$ denotes methyl, ethyl, isopropyl, sec-butyl, 2-methylpropyl, $CH(OR^5)CH_3$, $(CH_2)_4OR^5$, $CH_2SR^6$, $CH_2CH_2SCH_3$, $(CH_2)_4NR^7R^8$, $(CH_2)_3NHC(NH)(NH_2)$, $CH_2CO_2R^c$, $CH_2CH_2CO_2R^c$, $CH_2CONR^9R^{10}$, $CH_2CH_2CONR^9R^{10}$,

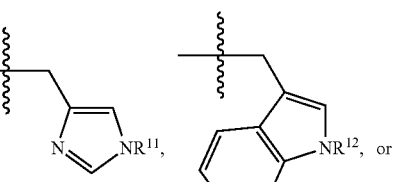

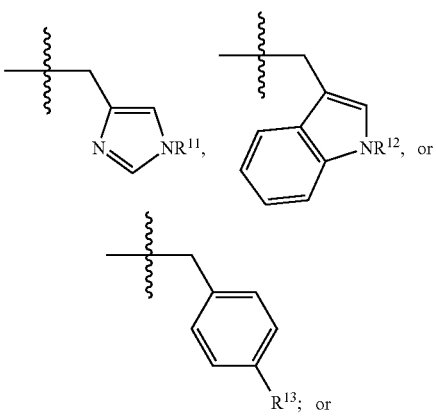

$R^g$ and $R^x$ may together form $-(CH_2)_3-$;

u denotes 0 or 1;

v denotes 0 or 1; and

M, A, R, $R^5$, $R^6$, $R^7$, $R^8$, $R^9$, $R^{10}$, $R^{11}$, $R^{12}$, $R^{13}$, $R^b$, $R^z$, and t are as defined for the compound of formula (Ia).

The M substituent in the compound of formula (Ic) can be replaced with a catalytic metal centre, such as Au(I). The present invention therefore also relates to a compound of formula (IIc') or (IIc'')

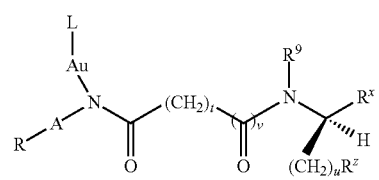

(IIc')

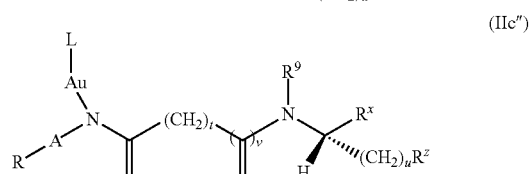

(IIc'')

wherein

L denotes $P(R^1)_3$, $S(R^2)_2$, $N(R^3)_3$ or

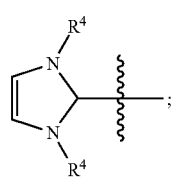

$R^1$ denotes $C_1$-$C_4$-alkyl, cyclohexyl or adamantyl; or phenyl optionally substituted with 1 to 5 $R^a$;

each $R^a$ independently denotes halogen, OH, $NO_2$, $C_1$-$C_4$-alkyl, $C_1$-$C_4$-alkoxy or $N(R^b)_2$;

each $R^2$ independently denotes $C_1$-$C_4$-alkyl or cyclohexyl;

each $R^3$ independently denotes $C_1$-$C_4$-alkyl or cyclohexyl;

each $R^4$ independently denotes $C_1$-$C_4$-alkyl, cyclohexyl or adamantyl; or phenyl optionally substituted with 1 to 5 $R^a$;

$R^z$ denotes $CO_2R^c$ or $CH_2P(R^{15})_2$;

$R^{15}$ both denote $R^1$; and

A, R, $R^b$, $R^c$, $R^g$, $R^x$, t, u and v are as defined for the compound of formula (Ic).

In further embodiments, the compounds of the present invention can utilise the N-terminus of an α- or β-amino acid as the coordinating atom. Thus, the present invention preferably relates to a compound of formula (Id') or (Id")

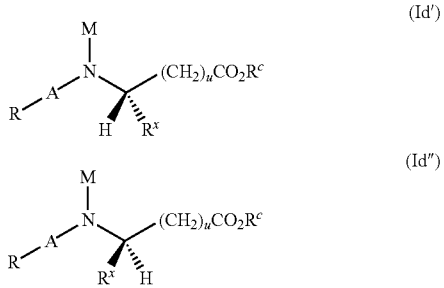

wherein $R^x$ denotes methyl, ethyl isopropyl, sec-butyl, 2-methylpropyl, $CH(OR^5)CH_3$, $(CH_2)_4OR^5$, $CH_2SR^6$, $CH_2CH_2SCH_3$, $(CH_2)_4NR^7R^8$, $(CH_2)_3NHC(NH)(NH_2)$, $CH_2CO_2R^c$, $CH_2CH_2CO_2R^c$, $CH_2CONR^9R^{10}$, $CH_2CH_2CONR^9R^{10}$,

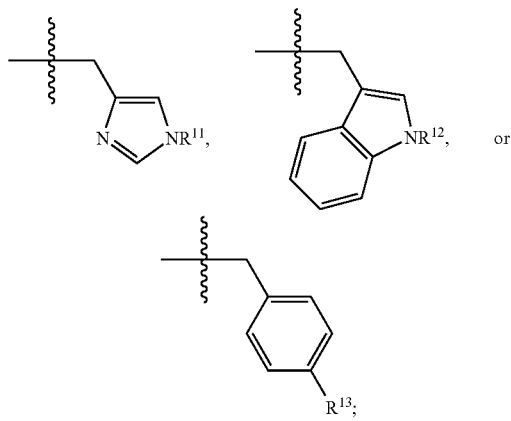

u denotes 0 or 1; and

M, A, R, $R^5$, $R^6$, $R^7$, $R^8$, $R^9$, $R^{10}$, $R^{11}$, $R^{12}$, $R^{13}$ and a $R^c$ are as defined for the compound of formula (Ia).

The M substituent in the compound of formula (Id) can be replaced with a catalytic metal centre, such as Au(I). The present invention therefore also relates to a compound of formula (IId') or (IId")

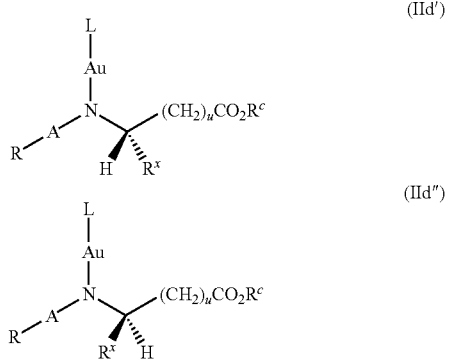

wherein

L denotes $P(R^1)_3$, $S(R^2)_2$, $N(R^3)_3$ or

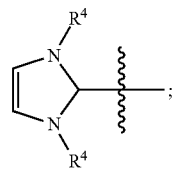

$R^1$ denotes $C_1$-$C_4$-alkyl, cyclohexyl or adamantyl; or phenyl optionally substituted with 1 to 5 $R^a$;

each $R^a$ independently denotes halogen, OH, $NO_2$, $C_1$-$C_4$-alkyl, $C_1$-$C_4$-alkoxy or $N(R^b)_2$;

each $R^2$ independently denotes $C_1$-$C_4$-alkyl or cyclohexyl;

each $R^3$ independently denotes $C_1$-$C_4$-alkyl or cyclohexyl;

each $R^4$ independently denotes $C_1$-$C_4$-alkyl, cyclohexyl or adamantyl; or phenyl optionally substituted with 1 to 5 $R^a$; and A, R, $R^c$, $R^x$ and u are as defined for the compound of formula (Id).

As noted above, in the compounds of formula (Ia), the C-terminal carboxylic acid may be replaced with a phosphine group denoted as $CH_2P(R^{15})_2$. This phosphine group may form part of a bidentate phosphine-containing ligand such as BINAP. In such embodiments, the compound of formula (Ia) actually contains two "$G_1NAR$" metal coordinating centres, and has the following generic structure:

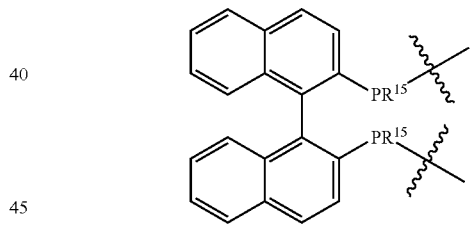

In the structure shown above, the third bonds from each phosphorus atom each bond to the remainder of a compound of formula (Ia), specifically to the carbon atom deriving from the C-terminus carboxylic acid in that compound. Since the phosphine atom contains three different groups, it is itself chiral. Moreover, the methodology described herein allows the formation of these BINAP derived ligands in an atropselective synthesis. In other words, the atropisomerism from the BINAP starting material may be retained during formation of the compound of formula $(Ia)_2$.

The compound of formula (IIa) described above also encompasses such BINAP-derived compounds, in which one or two gold atoms are complexed to the "NAR" and/or BINAP-phosphine ligands. Such compounds are sometimes denoted as compounds of formula $(IIa)_2$ herein.

Thus, the present invention preferably relates to a compound of formula (Ie') or (Ie")

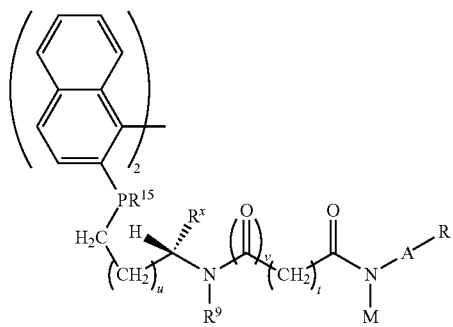
(Ie')

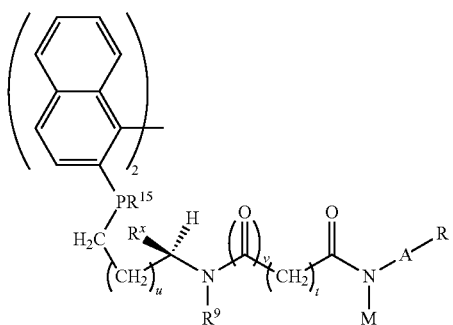
(Ie")

wherein $R^{15}$ is phenyl optionally substituted with 1-5 $R^a$;

$R^9$ denotes $R^b$;

u is 0 or 1;

v is 0 or 1;

t denotes an integer from 1 to 4;

$R^x$ denotes methyl, ethyl, isopropyl, sec-butyl, 2-methylpropyl, $CH(OR^5)CH_3$, $(CH_2)_4OR^5$, $CH_2SR^6$, $CH_2CH_2SCH_3$, $(CH_2)_4NR^7R^8$, $(CH_2)_3NHC(NH)(NH_2)$, $CH_2CO_2R^c$, $CH_2CH_2CO_2R^c$, $CH_2CONR^9R^{10}$, $CH_2CH_2CONR^9R^{10}$,

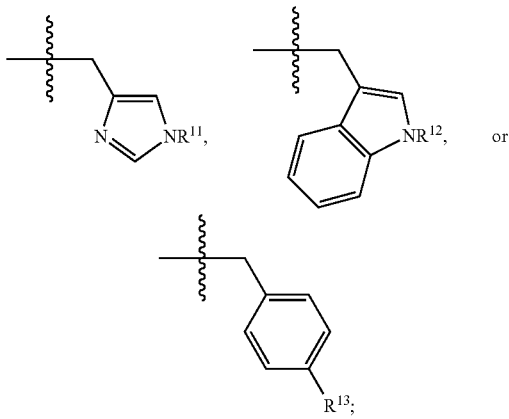

and

M, A, R, $R^5$, $R^6$, $R^7$, $R^8$, $R^9$, $R^{10}$, $R^{11}$, $R^{12}$, $R^{13}$, $R^a$, $R^b$ and $R^c$ are as defined for the compound of formula (Ia).

In the compound of formula (Ie), the atom denoted * corresponds to the equivalent carbon atom of the naphthyl ring in the 1,1' binaphthyl moiety.

Particularly preferred compounds of formula (Ie) are shown below:

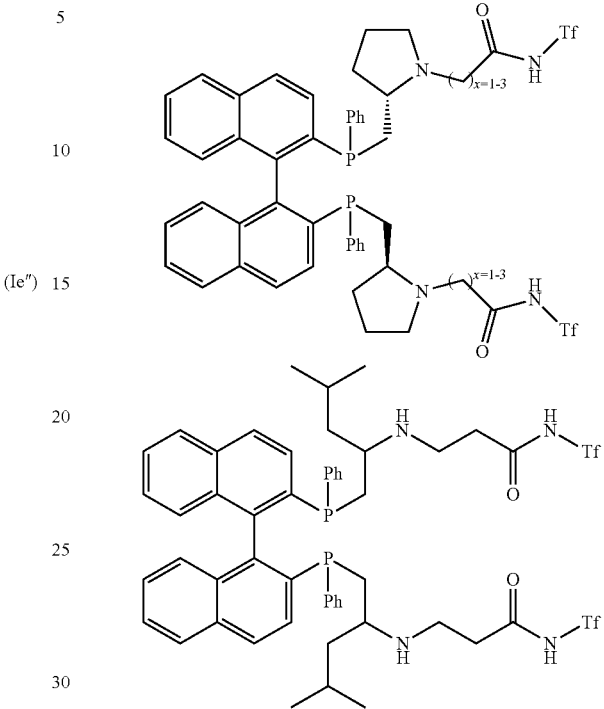

in which Tf corresponds to triflate($SO_2CF_3$).

The G substituent in the compound of formula (II) may contain a moiety that is capable of coordinating to a metal centre. In such embodiments, this moiety in the G substituent may replace the L substituent in the compound of formula (II) to form a macrocycle containing the Au metal.

Thus, the present invention is preferably directed to a compound of formula (IIIa') or (IIIc")

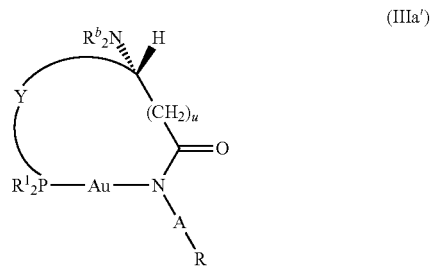
(IIIa')

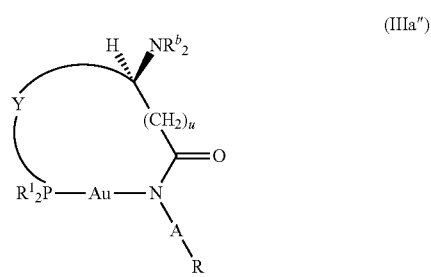
(IIIa")

wherein
Y—P(R$^1$)$_2$ denotes

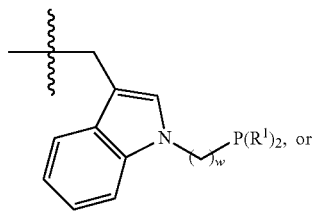

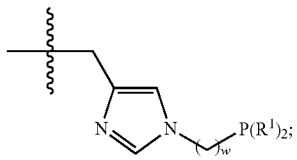

w denotes an integer from 1 to 4;
u denotes 0 or 1; and
A, R, R$^1$ and R$^b$ are as defined for the compound of formula (Ia).

Preferably, the present invention is directed to a compound of formula (IIIb') or (IIIb'')

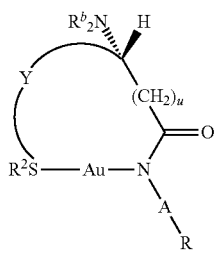
(IIIb')

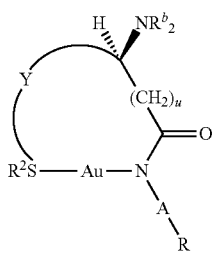
(IIIb'')

wherein
Y—SR$^2$ denotes CH$_2$SR$^2$, CH$_2$CH$_2$SCH$_3$,

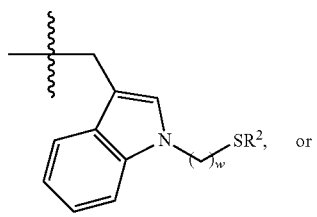

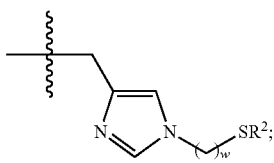

w denotes an integer from 1 to 4;
u denotes 0 or 1; and
A, R, R$^2$ and R$^b$ are as defined for the compound of formula (Ia).

Preferably, the present invention is directed to a compound of formula (IIIc') or (IIIc'')

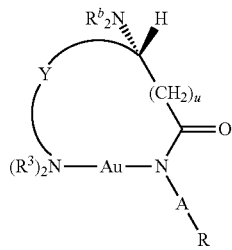
(IIIc')

(IIIc'')

wherein
Y—N(R$^3$)$_2$ denotes CH$_2$CH$_2$CH$_2$N(R$^3$)$_2$,

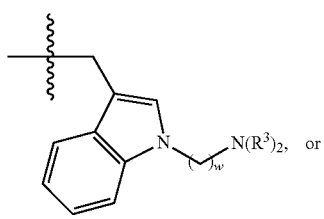

w denotes an integer from 1 to 4;
u denotes 0 or 1; and
A, R, R$^3$ and R$^b$ are as defined for the compound of formula (Ia).

Preferably, the present invention relates to a compound of formula (IIId') or (IIId")

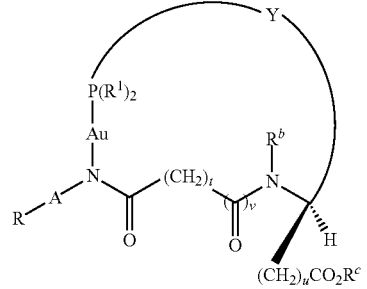
(IIId')

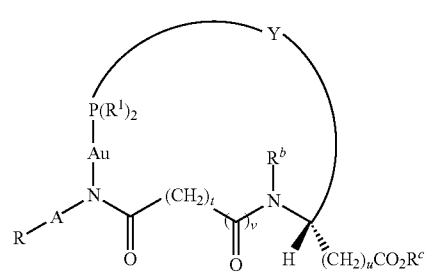
(IIId")

wherein
Y—P(R')$_2$ denotes

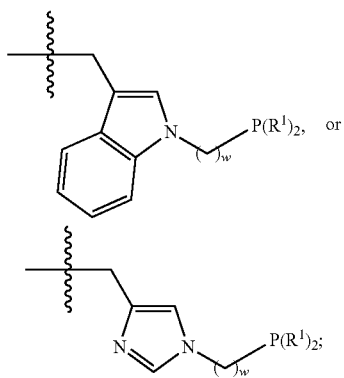

u denotes 0 or 1;
v denotes 0 or 1;
w denotes an integer from 1 to 4; and
A, R, R$^1$, R$^b$, R$^c$ and t are as defined for the compound of formula (Ia), Preferably, the present invention relates to a compound of formula (IIIe') or (IIIe")

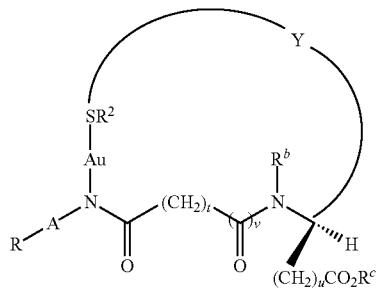
(IIIe')

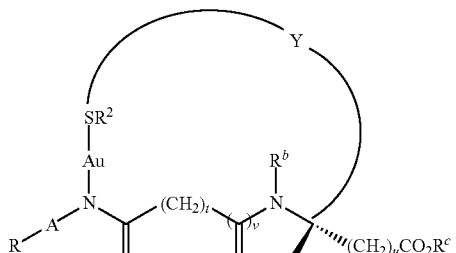
(IIIe")

wherein
Y—SR$^2$ denotes CH$_2$SR$^2$, CH$_2$CH$_2$SCH$_3$,

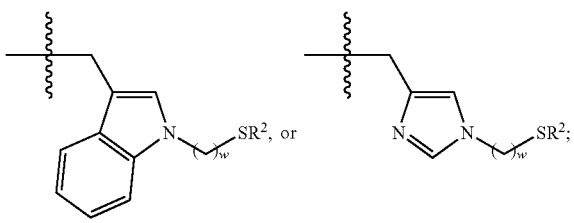

u denotes 0 or 1;
v denotes 0 or 1;
w denotes an integer from 1 to 4; and
A, R, R$^2$, R$^b$, R$^c$ and t are as defined for the compound of formula (Ia).

Preferably, the present invention relates to a compound of formula (IIIf') or (IIIf")

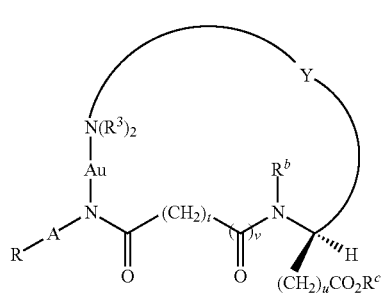
(IIIf')

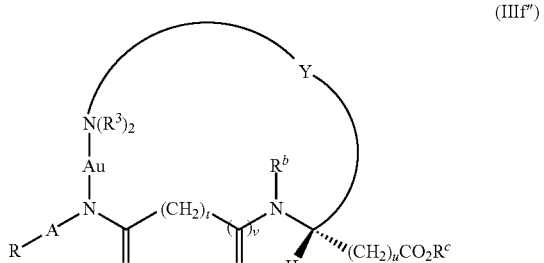
(IIIf")

wherein
Y—N(R³)₂ denotes CH₂CH₂CH₂N(R³)₂,

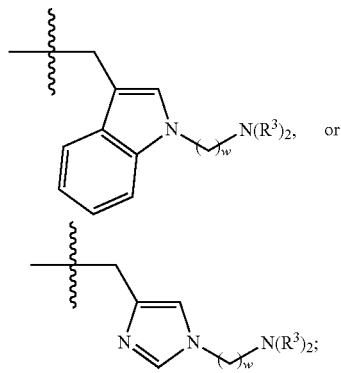

u denotes 0 or 1;
v denotes 0 or 1;
w denotes an integer from 1 to 4; and
A, R, R³, R$^b$, R$^d$ and t are as defined for the compound of formula (Ia).

As noted above, the present invention allows for the C-terminus carboxylic acid group to be replaced with a phosphine group. Thus, the present invention preferably relates to a compound of formula (IIIg') or (IIIg")

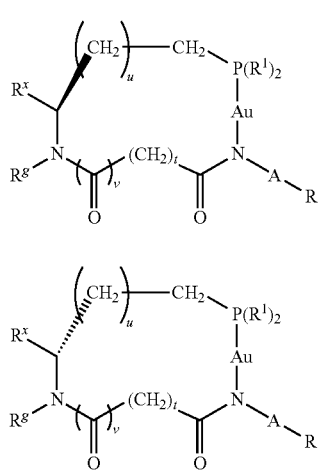

wherein
u denotes 0 or 1;
v denotes 0 or 1;
R⁹ denotes R$^b$;
R$^x$ denotes methyl, ethyl, isopropyl, sec-butyl, 2-methylpropyl, CH(OR⁵)CH₃, (CH₂)₄OR⁵, CH₂SR⁶, CH₂CH₂SCH₃, (CH₂)₄NR⁷R⁸, (CH₂)₃NHC(NH)(NH₂), CH₂CO₂R$^c$, CH₂CH₂CO₂R$^c$, CH₂CONR⁹R¹⁰, CH₂CH₂CONR⁹R¹⁰,

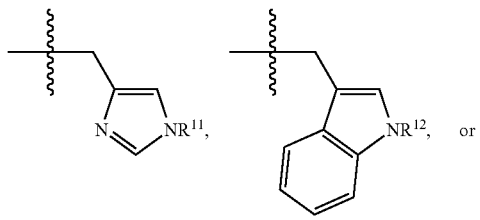

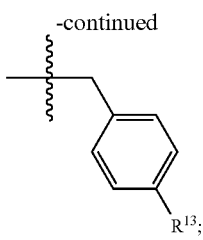

or
R⁹ and Rx may together form —(CH₂)₃—;
R¹¹ denotes H, C₁-C₄-alkyl;
R¹² denotes H, C₁-C₄-alkyl; and
M, t, A, R, R¹, R⁵, R⁶, R⁷, R⁸, R⁹, R¹⁰, R¹³, R$^b$ and R$^c$ are as defined for the compound of formula (Ia).

As noted above, if the compound of formula (I) contains two coordinating groups, that is a coordinating group on the G substituent in addition to the N(AR)G coordinating group, it is possible to form macrocyclic compounds in which the compound of formula (I) chelates to the Au metal centre. It is also possible to form macrocyclic compounds containing two Au metal atoms and two formula (I) ligands, wherein each compound of formula (I) bonds to both metal atoms and the ligands are arranged "top-to-tail" as shown below:

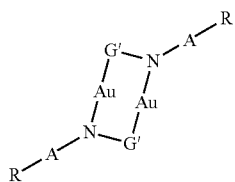

For ease of reference, this can be represented as a compound of formula (IV)

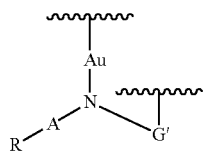

Thus, the present invention preferably relates to a compound of formula (IVa') or (IVa")

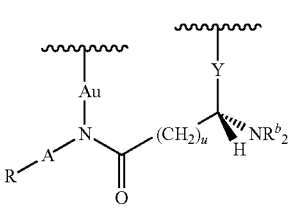

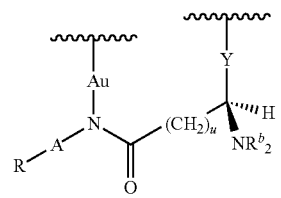

wherein

Y denotes

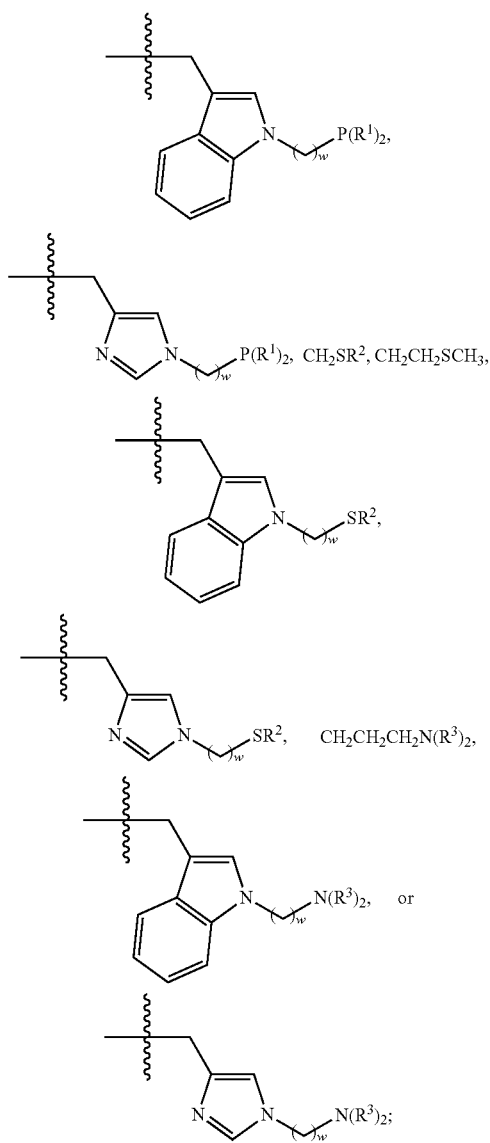

w denotes an integer from 1 to 4;

u denotes 0 or 1; and

A, R, $R^1$, $R^2$, $R^3$ and $R^b$ are as defined for the compound of formula (Ia).

Preferably, the present invention relates to a compound of formula (IVb') or (IVb'')

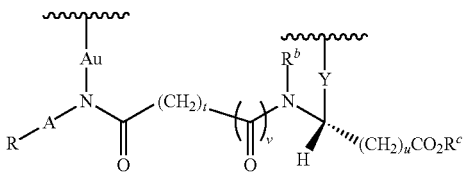
(IVb')

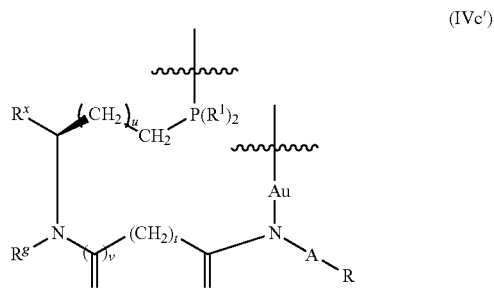
(IVb'')

wherein t denotes an integer from 1 to 4;

v denotes 0 or 1;

$R^c$ denotes $C_1$-$C_4$-alkyl, or $PG^{ac}$; and

A, R, $R^b$, u and Y are as defined for the compound of formula (IVa).

Preferably, the present invention relates to a compound of formula (IVc') or (IVc'')

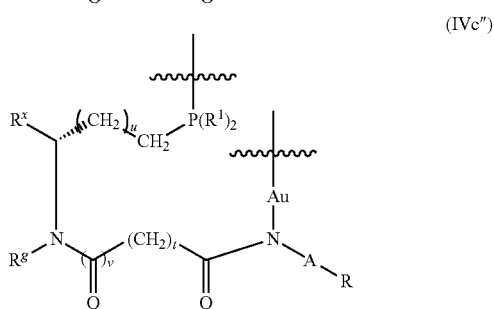
(IVc')

(IVc'')

wherein u denotes 0 or 1;

v denotes 0 or 1;

$R^g$ denotes $R^b$;

$R^x$ denotes methyl, ethyl, isopropyl, sec-butyl, 2-methyl-propyl, $CH(OR^5)CH_3$, $(CH_2)_4OR^5$, $CH_2SR^6$, $CH_2CH_2SCH_3$, $(CH_2)_4NR^7R^8$, $(CH_2)_3NHC(NH)(NH_2)$, $CH_2CO_2R^c$, $CH_2CH_2CO_2R^c$, $CH_2CONR^9R^{10}$, $CH_2CH_2CONR^9R^{10}$,

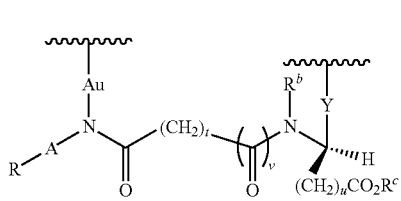

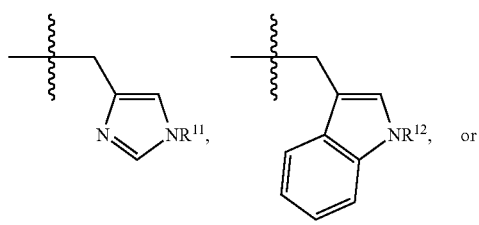

-continued

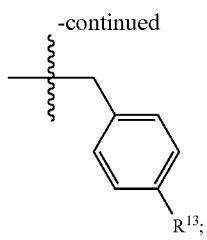

or $R^9$ and $R^x$ may together form —$(CH_2)_3$—; and

M, t, A, R, $R^1$, $R^5$, $R^6$, $R^7$, $R^8$, $R^9$, $R^{10}$, $R^{11}$, $R^{12}$, $R^{13}$, $R^b$ and $R^c$ are as defined for the compound of formula (Ia).

Preferably, in the compounds of formula (I), (Ia), (Ib), (Ic), (Id), (Ie), (II), (IIa), (IIb), (IIc), (IId), (III), (IIIa), (IIIb), (IIIc), (IIId), (IIIe), (IIIf), (IIIg), (IVa), (IVb) and (IVc), A denotes $SO_2$ or C(=O).

Preferably, in the compounds of formula (I), (Ia), (Ib), (Ic), (Id), (Ie), (II), (IIa), (IIb), (IIc), (IId), (III), (IIIa), (IIIb), (IIIc), (IIId), (IIIe), (IIIf), (IIIg), (IVa), (IVb) and (IVc), R denotes $C_1$-$C_6$-alkyl, $C_1$-$C_6$-fluoroalkyl; or phenyl optionally substituted with 1 to 5 $R^a$.

Preferably, in the compounds of formula (I), (Ia), (Ib), (Ic), (Id), (Ie), (II), (IIa), (IIb), (IIc), (IId), (III), (IIIa), (IIIb), (IIIc), (IIId), (IIIe), (IIIf), (IIIg), (IVa), (IVb) and (IVc), A-R denotes $SO_2CH_3$, $SO_2C_1$-$C_6$-perfluoroalkyl, $SO_2C_6H_5Me$, $SO_2C_6H_5NO_2$ or $COC_6H_5Br$.

Preferably, in the compounds of formula (I), (Ia), (Ib), (Ic), (Id), (Ie), (II), (IIa), (IIb), (IIc), (IId), (III), (IIIa), (IIIb), (IIIc), (IIId), (IIIe), (IIIf), (IIIg), (IIIh), (IVa), (IVb) and (IVc), A-R denotes $SO_2CH_3$, $SO_2CF_3$, $SO_2C_6H_5Me$, $SO_2C_6H_5NO_2$ or $COC_6H_5Br$.

Preferably, in the compounds of formula (II), (IIa), (IIb), (IIc), and (IId),

L denotes $P(R^1)_3$, $S(R^2)_2$ or $N(R^3)_3$.

Preferably, in the compounds of formula (II), (IIa), (IIb), (IIc), and (IId),

L denotes $P(R^1)_3$.

Preferably, in the compounds of formula (II), (IIa), (IIb), (IIc), and (IId),

L denotes $P(R^1)_3$; and $R^1$ denotes $CH_3$, $C_2H_5$; or phenyl optionally substituted with 1 to 5 $R^a$.

Preferably, in the compounds of formula (II), (IIa), (IIb), (IIc), and (IId),

L denotes $P(CH_3)_3$, $P(C_2H_5)_3$ or $PPh_3$.

Preferably, in the compounds of formula (II), (IIa), (IIb), (IIc), and (IId),

L denotes $P(R^1)_3$; and $R^1$ denotes phenyl optionally substituted with 1 to 5 $R^a$.

Preferably, in the compounds of formula (II), (IIa), (IIb), (IIc), and (IId),

L denotes $PPh_3$.

Preferably, in the compounds of formula (I), (Ia), (Ib), (Ic), (Id) and (Ie),

M denotes hydrogen or an alkali metal.

Preferably, in the compounds of formula (I), (Ia), (Ib), (Ic), (Id) and (Ie),

M denotes hydrogen.

Preferably, in the compounds of formula (IIIa), (IIId), (IIIg), (IVa), (IVb) and (IVc), $R^1$ denotes $CH_3$, $C_2H_5$; or phenyl optionally substituted with 1 to 5 $R^a$.

Preferably, in the compounds of formula (IIIa), (IIId), (IIIg), (IVa), (IVb) and (IVc), $R^1$ denotes $CH_3$ or phenyl.

Preferably, in the compounds of formula (IIIa), (IIId), (IIIg), (IVa), (IVb) and (IVc), $R^1$ denotes phenyl.

Preferably, in the compounds of formula (Ia), (Ib), (Ic), (Id), (Ie), (IIa), (IIb), (IIc), (IId), (III), (IIIb), (IIIe), (IVa), (IVb) and (IVc), $R^2$ denotes $C_1$-$C_4$-alkyl.

Preferably, in the compounds of formula (Ia), (Ib), (Ic), (Id), (Ie), (IIa), (IIb), (IIc), (IId), (III), (IIIb), (IIIe), (IVa), (IVb) and (IVc), $R^2$ denotes methyl.

Preferably, in the compounds of formula (Ia), (Ib), (Ic), (Id), (Ie), (IIa), (IIb), (IIc), (IId), (III), (IIIc), (IIIf), (IVa), (IVb) and (IVc), $R^3$ denotes $C_1$-$C_4$-alkyl.

Preferably, in the compounds of formula (Ia), (Ib), (Ic), (Id), (Ie), (IIa), (IIb), (IIc), (IId), (III), (IIIc), (IIIf), (IVa), (IVb) and (IVc), $R^3$ denotes methyl.

Preferably, in the compounds of formula (Ia), (Ib), (Ic), (Id), (Ie), (IIa), (IIb) (IIc), (IId), and (IIIg), $R^5$ denotes H or $C_1$-$C_4$-alkyl.

Preferably, in the compounds of formula (Ia), (Ic), (Ie), (IIa), (IIc), (IIId), (IIIe), (IIIf), (IIIg), (IVa), (IVb), and (IVc)

v denotes 1; and t denotes an integer from 2 to 4.

Preferably, in the compounds of formula (Ia), (Ic), (Ie), (IIa), (IIc), (IIId), (IIIe), (IIIf), (IIIg), (IVa), (IVb), and (IVc)

v denotes 1; and t denotes 2.

Preferably, in the compounds of formula (Ia), (Ic), (Ie), (IIa), (IIc), (IIId), (IIIe), (IIIf), (IIIg), (IVa), (IVb), and (IVc), v denotes 0.

Preferably, in the compounds of formula (Ia), (Ib), (Ic), (Id), (Ie), (IIa), (IIb), (IIc), (IId), (IIIa), (IIIb), (IIIc), (IIId), (IIIe), (IIIf), (IIIg), (IVa), (IVb) and (IVc), $R^b$ denotes hydrogen, $C_1$-$C_4$-alkyl, or $(CH_2)_{1-4}CO_2CH_3$.

Preferably, in the compounds of formula (Ia), (Ib), (Ic), (Id), (Ie), (IIa), (IIb), (IIc), (IId), (IIIa), (IIIb), (IIIc), ((IId), (IIIe), (IIIf), (IIIg), (IVa), (IVb) and (IVc), $R^b$ denotes hydrogen or methyl.

Preferably, in the compounds of formula (Ia), (Ib), (Ic), (Id), (Ie), (IIa), (IIb), (IIc), (IId), ((IId), (IIIe), (IIIf), (IIIg), (IVb) and (IVc), $R^c$ denotes $C_1$-$C_4$-alkyl.

Preferably, in the compounds of formula (Ia), (Ib), (Ic), (Id), (Ie), (IIa), (IIb), (IIc), (IId), ((IId), (IIIe), (IIIf), (IIIg), (IVb) and (IVc), $R^c$ denotes methyl.

Preferably, in the compounds of formula (Ia), (Ib), (Ic), (Id), (Ie), (IIa), (IIb), (IIc), (IId), (IIIa), (IIIb), (IIIc), (IIId), (IIIe), (IIIf), (IIIg), (IVa), (IVb) and (IVc), u is 0.

Preferably, in the compounds of formula (Ia), (Ib), (Ic), (Id), (Ie), (IIa), (IIb), (IIc), (IId), (IIIa), (IIIb), (IIIc), (IIId), (IIIe), (IIIf), (IIIg), (IVa), (IVb) and (IVc), u is 1

Preferably, in the compounds of formula (IIIa), (IIIb), (IIIc), (IIId), (IIIe), (IIIf), (IVa), and (IVb), w is 1 or 2.

Preferably, in the compounds of formula (Ia), (Ib), (Ic), (Id), (Ie), (IIa), (IIb), (IIc), (IId), (IIIg) and (IVc)

$R^{11}$ denotes H or $C_1$-$C_4$-alkyl; and $R^{12}$ denotes H or $C_1$-$C_4$-alkyl.

Preferably, in the compounds of formula (Ia) and (IIa), $G^1$ denotes a bond; and $R^y$ denotes $(CH_2)CO_2R^c$.

Preferably, in the compounds of formula (Ia) and (IIa),
$G^1$ denotes —C(=O)(CH$_2$)$_u$—; and
$R^y$ denotes N(R$^b$)$_2$.

Preferably, in the compounds of formula (Ia) and (IIa),
$G^1$ denotes —C(=O)—(CH$_2$)$_t$-G$^2$; and
$G^2$ denotes (C(=O))$_v$NR$^g$.

Preferably, in the compounds of formula (Ia) and (IIa),
$G^1$ denotes —C(=O)—(CH$_2$)$_t$-G$^2$;
$G^2$ denotes (C(=O))$_v$NR$^g$; and
$R^y$ denotes (CH$_2$)$_u$CO$_2$R$^c$.

Preferably, in the compounds of formula (Ia) and (IIa),
$G^1$ denotes —C(=O)—(CH$_2$)$_t$-G$^2$;
$G^2$ denotes (C(=O))$_v$NR$^g$; and
$R^y$ denotes CH$_2$P(R$^{15}$)$_2$.

Preferably, in the compounds of formula (Ia), (Ib), (Ic), (Id), (Ie), (IIa), (IIb), (IIc), (IId), (IIIg), and (IVc),
$R^x$ denotes methyl, ethyl, isopropyl, sec-butyl, 2-methyl-propyl, CH(OR$^5$)CH$_3$, (CH$_2$)$_4$OR$^5$, CH$_2$SR$^6$, CH$_2$CH$_2$SCH$_3$, (CH$_2$)$_4$NR$^7$R$^8$, CH$_2$CO$_2$R$^c$, CH$_2$CH$_2$CO$_2$R$^c$, CH$_2$CONR$^9$R$^{10}$, CH$_2$CH$_2$CONR$^9$R$^{10}$,

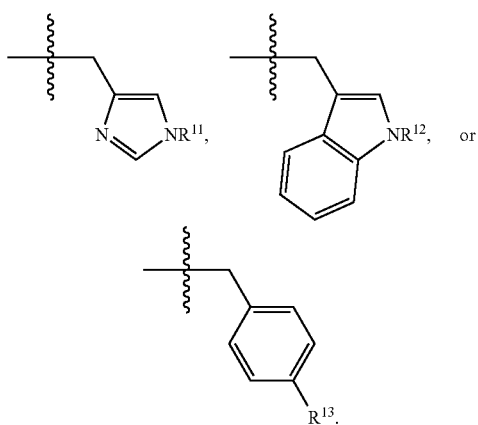

Preferably, in the compounds of formula (Ia), (Ib), (Ic), (Id), (Ie), (IIa), (IIb), (IIc), (IId), (IIIg), and (IVc),
$R^x$ denotes methyl, ethyl, isopropyl, sec-butyl, 2-methyl-propyl,

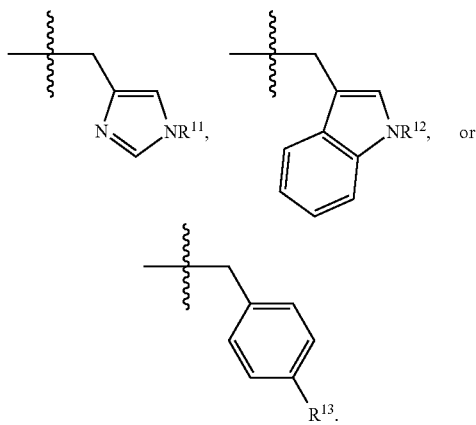

Preferably, in the compounds of formula (Ia), (Ib), (Ic), (Id), (Ie), (IIa), (IIb), (IIc), (IId), (IIIg), and (IVc),
$R^x$ denotes methyl, ethyl, isopropyl, sec-butyl, 2-methyl-propyl, CH(OR$^5$)CH$_3$, (CH$_2$)$_4$OR$^5$, CH$_2$SR$^6$, CH$_2$CH$_2$SCH$_3$, (CH$_2$)$_4$NR$^7$R$^8$,

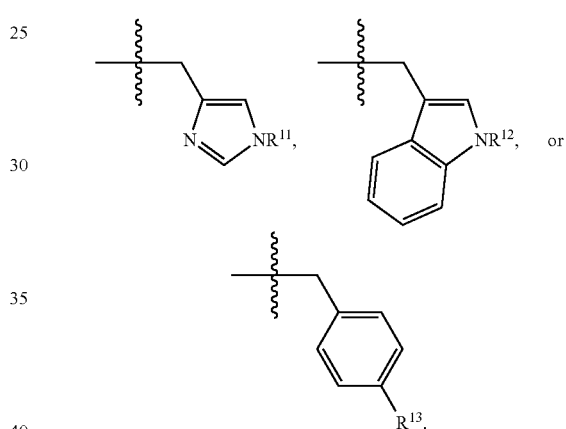

Preferably, in the compounds of formula (Ia), (Ib), (Ic), (Id), (Ie), (IIa), (IIb), (IIc), (IId), (IIIg), and (IVc),
$R^x$ denotes

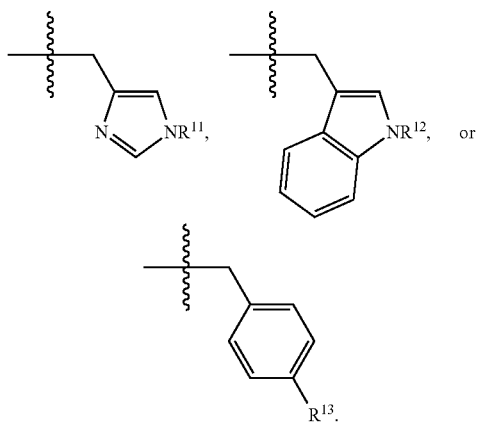

Preferably, in the compounds of formula (Ia), (Ib), (Ic), (Id), (Ie), (IIa), (IIb), (IIc), (IId), (IIIg), and (IVc),
$R^x$ denotes methyl, ethyl, isopropyl, sec-butyl, 2-methyl-propyl, CH(OR$^5$)CH$_3$, (CH$_2$)$_4$OR$^5$, CH$_2$SR$^6$, CH$_2$CH$_2$SCH$_3$, (CH$_2$)$_4$NR$^7$R$^8$,

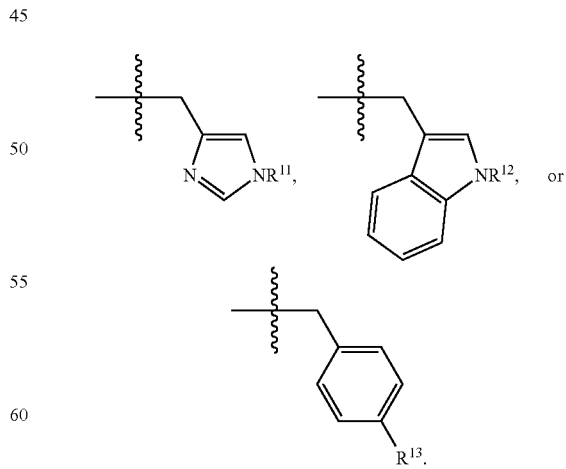

Preferably, in the compounds of formula (Ia), (Ib), (Ic), (Id), (Ie), (IIa), (IIb), (IIc), (IId), (IIIg), and (IVc),
$R^x$ denotes methyl, isopropyl, sec-butyl or 2-methyl-propyl.

Preferably, in the compounds of formula (Ia), (IIa), (Ic) and (IIc),
$R^z$ denotes $CO_2R^c$.
Preferably, in the compounds of formula (Ia), (IIa), (Ic) and (IIc),
$R^z$ denotes $CH_2P(R^{15})_2$.
Preferably, in the compounds of formula (Ia), (IIa), (Ic) and (IIc),
$R^z$ denotes $CH_2P(R^{15})_2$; and
$R^{15}$ both denote $R^1$.
Preferably, in the compounds of formula (II), (IIa), (IIb), (IIc), (IId), (IIIa), (IIIb), (IIIc), (IIId), (IIIe), (IIIf), (IIIg), (IVa), (IVb), and (IVc),
the Au atom is Au(I).

It is to be understood that where the preferred embodiments mentioned above are not mutually exclusive, they can be combined with one another. For example, the skilled person would understand that the above preferred embodiments in which $R^z$ denotes $CO_2R^c$ can be combined with the preferred embodiments in which $R^c$ denotes $C_1$-$C_4$-alkyl or methyl. The same holds true for the other non-mutually exclusive preferred embodiments mentioned above. The skilled person would understand which embodiments where mutually exclusive and would thus readily be able to determine the combinations of preferred embodiments that are contemplated by the present application.

As used herein, "alkyl" or "alkylene" is intended to include both branched and straight-chain saturated aliphatic hydrocarbon groups having the specified number of carbon atoms, preferably having 6 carbon atoms. For example, "$C_1$-$C_6$ alkyl" is intended to include $C_1$, $C_2$, $C_3$, $C_4$, $C_5$ and $C_6$ alkyl groups. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "cycloalkyl" refers to cyclized alkyl groups, including mono-, bi- or poly-cyclic ring systems. Example cycloalkyl groups include, but are not limited to, cyclopropyl, cyclobutyl, cyclopentyl, cyclohexyl, norbornyl, adamantyl and the like. Branched cycloalkyl groups such as 1-methylcyclopropyl and 2-methylcyclopropyl are included in the definition of "cycloalky".

"Halo" or "halogen" as used herein refers to fluoro, chloro, bromo, and iodo, preferably fluoro and chloro.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Alkoxy" represents an alkyl group as defined above with the indicated number of carbon atoms attached through an oxygen bridge. For example, "$C_1$-$C_4$-alkoxy" is intended to include $C_1$, $C_2$, $C_3$, and $C_4$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy.

As used herein, the term "aryl" or "aromatic residue", is intended to mean an aromatic moiety containing, if specified, the specified number of carbon atoms; for example phenyl or naphthyl.

As described above, protecting groups may be present in the compounds of the present invention. The use of protecting groups is well known in the art (see for example, T. W. Greene and P. G. M. Wuts, Protective Groups in Organic Synthesis, 3rd Edn., John Wiley & Sons). The skilled person will be aware of particular groups available for protecting amine, amide, carboxylic acid and alcohol groups, and the conditions under which protection and deprotection can occur. Any suitable protecting groups may be present in the compounds of the invention, either to aid in the synthesis of the compounds of formula I, or to prevent unwanted side reactions occurring with reactive side groups in the compounds of formulae II and III.

Suitable protecting groups for an imine include carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn) group, p-methoxybenzyl (PMB), 3,4-dimethoxybenzyl (DMPM), p-methoxyphenyl (PMP) group, tosyl (Ts), nosyl (Ns) and other sulfonamides.

Suitable protecting groups for a carboxylic acid include benzyl esters, silyl esters, orthoesters and oxazoline.

Suitable protecting groups for an alcohol include acetyl (Ac) benzoyl, benzyl (Bn), β-methoxyethoxymethyl ether (MEM), dimethoxytrityl [bis-(4-methoxyphenyl)phenylmethyl, DMT]methoxymethyl ether (MOM) methoxytrityl[(4-methoxyphenyl)diphenylmethyl, MMT), p-methoxybenzyl ether (PMB), methylthiomethyl ether, pivaloyl (Piv), tetrahydropyranyl (THP), trityl (triphenylmethyl, Tr), silyl ethers such as trimethylsilyl (TMS), tert-butyldimethylsilyl (TBDMS), tert-butyldimethylsilyloxymethyl (TOM), and triisopropylsilyl (TIPS) ethers), methyl ethers and ethoxyethyl ethers (EE).

The compounds of the invention may be synthesised from amino acids using a variety of synthetic strategies. For example, a typical synthetic routes are shown in the following schemes:

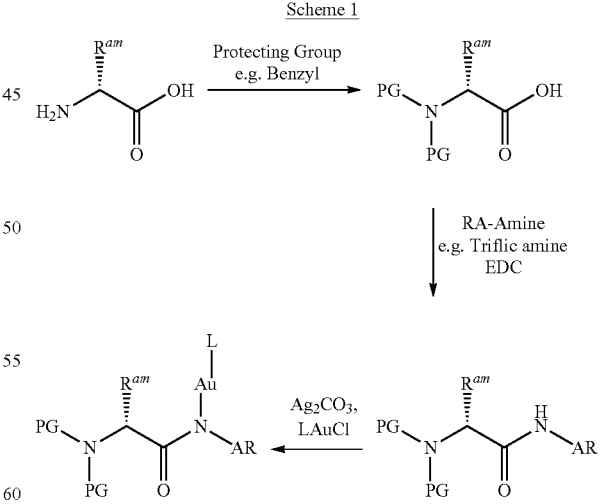

Scheme 1

The synthesis in Scheme 1 can be modified to introduce different functionalities onto the amino acid nitrogen atom, as shown in Schemes 2:

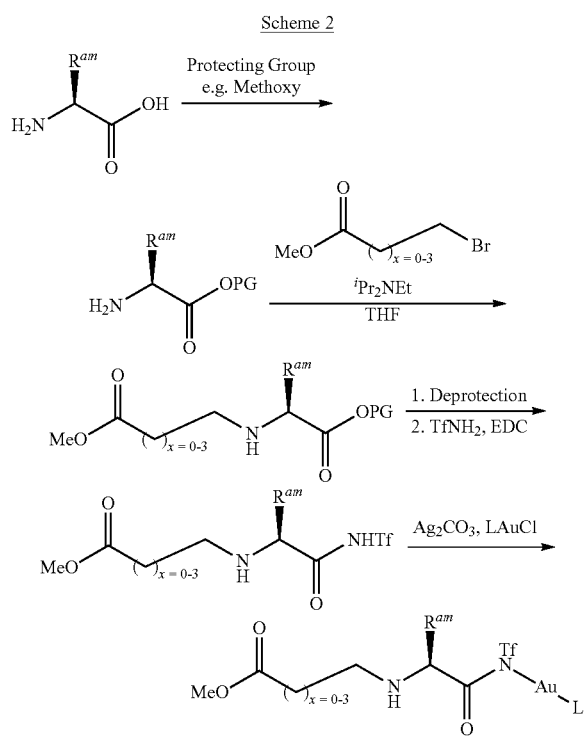
Protection of the carboxylic acid can also allow functionalisation of the amino acid nitrogen to allow coordination to a metal centre, either directly (Scheme 3) or via a linker group (Scheme 4):
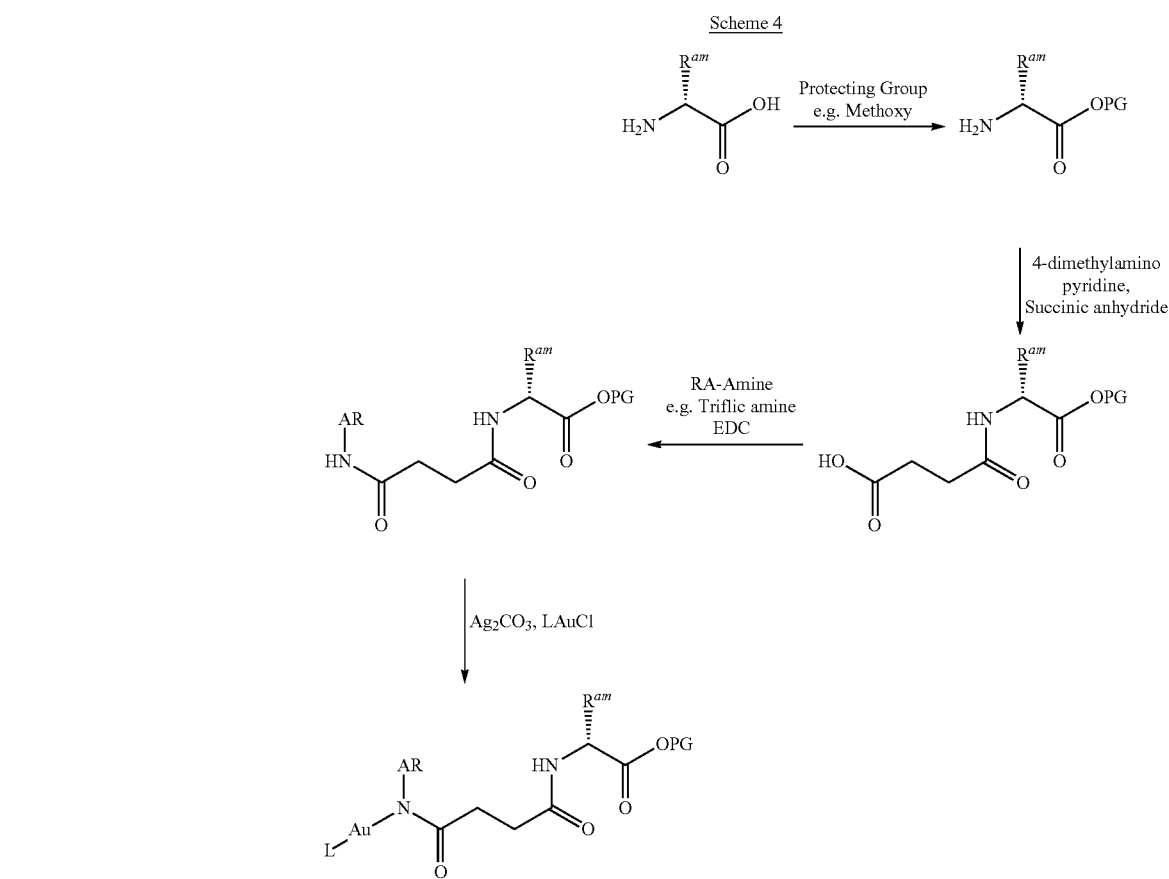

The carboxylic acid moiety in the amino acid may also be removed (for example with lithium aluminium hydride (LAN)) to allow functionalisation with a phosphine moiety, as shown in Scheme 5:

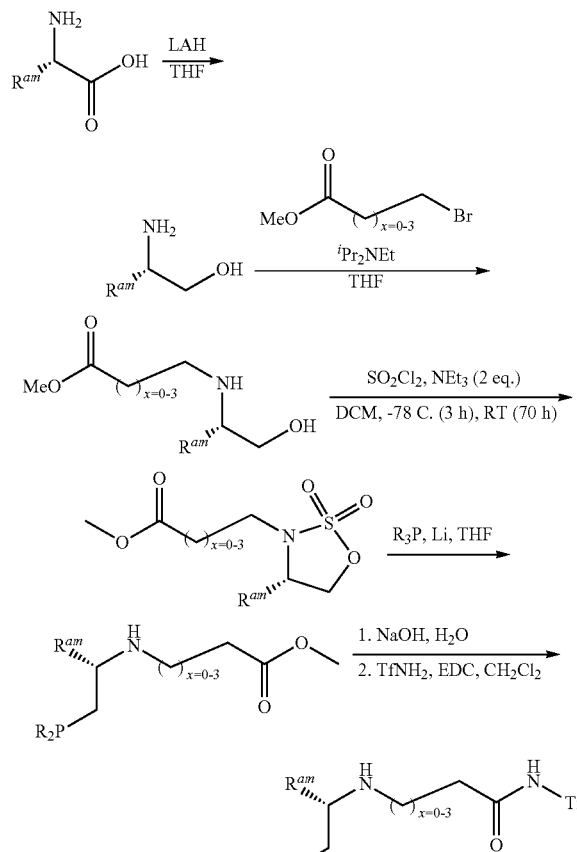

The methodology in Scheme 5 is in principle possible using any amino acid. However, it is preferable to use those an amino acid that does not contain a carboxylic acid in the side chain so as to avoid competing reactions in the final step.

An example of a typical synthetic route according to Scheme 5 is shown below in Scheme 6:

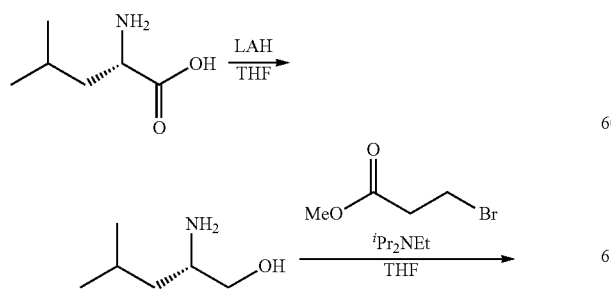

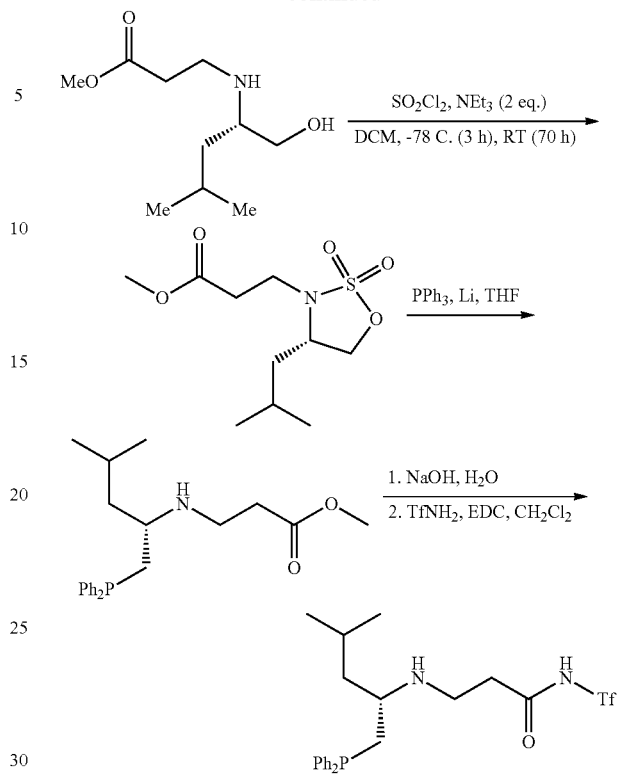

This methodology may be adapted to introduce other types of phosphine-containing ligands, including BINAP and related bidentate phosphine ligands. A typical synthetic route according to this methodology is shown below in Scheme 7:

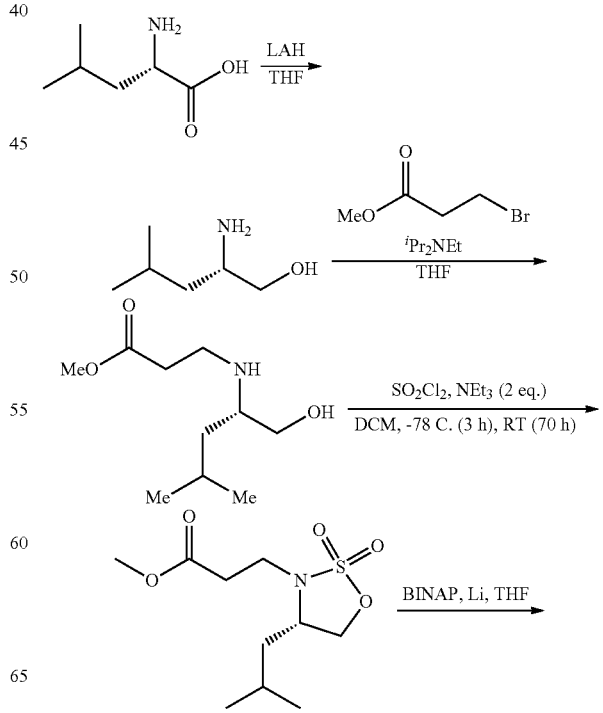

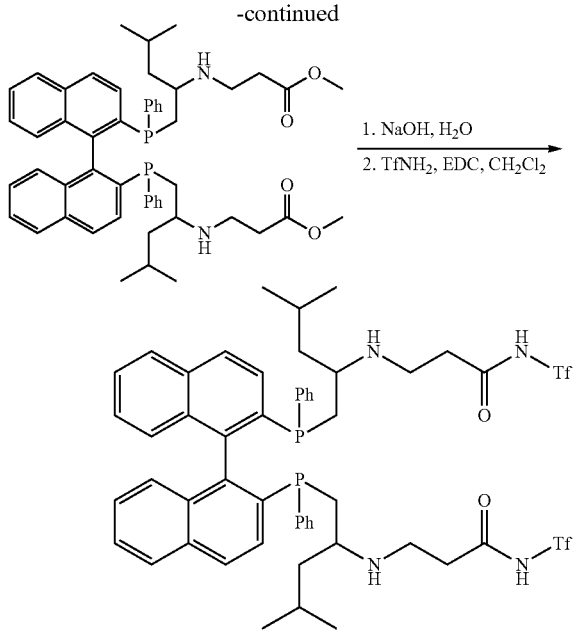

In the above schemes, $R^{am}$ corresponds to an amino acid side chain, which may be protected as necessary. While the above schemes are shown with respect to α-L-amino acids, the methodologies described would be equally applicable to β and/or D-amino acids. The skilled person would also know how to modify the above synthetic routes to incorporate other functionalities into the compounds of the invention. For example, while the AR moiety is typically shown to be derived from triflic acid, it would be trivial for the skilled person to adapt the above synthetic schemes to incorporate other functional groups at this position. Thus, using benzyl chloride in place of trifluoromethane sulfonic anhydride in Scheme 3 would functionalise the compound with AR denoting PhC=O in place of $CF_3SO_2$.

The methodology disclosed in Scheme 7 forms a further aspect of the present invention that can be used to synthesise atropisomerically enriched rotationally hindered ligands. During the lithiation step to functionalise the BINAP ligand, a chiral centre is selectively formed at the phosphorus atom in a stereospecific manner. Reaction of phenylphosphines with alkali metals is known to lead to cleavage of the P-aryl bond. In the case of BINAP, there are numerous possible outcomes to the reaction. For example, one or both phosphorus atoms could be metallated, or the metal may lead to cleavage of the P-naphthyl bond. Moreover, reaction of the metallated phosphorus with an electrophile or transition metal could lead to the formation of a chiral phosphorus atom (i.e. the phosphorus atom has three different substituents after reaction with the electrophile). As there are two phosphorus atoms, the resultant mixture potentially contains numerous chiral compounds depending on which phenyl is replaced, and whether one or both phosphorus atoms are metallated. As BINAP itself has axial chirality, the reaction can potentially lead to a large number of stereoisomers being formed.

The mixture obtained after reaction of atropisomerically enriched BINAP with sodium shows a number of peaks in the phosphorus NMR. Thus, the compound formed contains various stereoisomers. Further reaction with an electrophile leads to these stereoisomers being "trapped", such that the resultant product also comprises a number of stereoisomers. The resultant stereoisomers must be separated using stereoselective resolution such as precipitation with a chiral counterion, chiral HPLC or the like. Such processes are time consuming and unpredictable.

The BINAP process of the present, invention uses lithium to cleave the P-phenyl bond. The applicant has found that the compound formed by lithiating atropisomerically pure BINAP shows only one peak in the phosphorus NMR.

The BINAP process of the present invention therefore allows chirality to be introduced at a phosphine atom contained in a bidentate phosphine ligand having resolvable atropisomers. This is the case even if the phosphine ligand has axial chirality, i.e. it does not contain any stereogenic centres.

Thus, a further aspect of the present invention (referred to herein as the BINAP process) relates to a process for forming a ligand containing a chiral phosphorus atom, said process comprising the steps of:
a) reacting a bidentate, rotationally hindered diphenylphosphine-containing ligand with lithium metal in a non-reactive solvent; and
b) reacting the product formed with an electrophile or a transition metal complex.

As the lithiation reaction can be quite slow, the electrophile or transition metal complex is preferably not added until the lithiation reaction is complete. Completion of the lithiation reaction may be monitored by $^{31}$P-NMR. Thus, step (b) in the BINAP process of the present invention is preferably performed once there is a consistent $^{31}$P-NMR spectra of the product of step a).

Preferably, step a) in the BINAP process of the present invention comprises reacting a bidentate, rotationally hindered diphenylphosphine-containing ligand with lithium metal in a non-reactive solvent for at least 1 hour, more preferably for at least 2 hours, more preferably for at least 3 hours, more preferably for at least 4 hours, more preferably for at least 5 hours, more preferably for at least 6 hours, more preferably for at least 8 hours, morci, preferably for at least 10 hours, more preferably for at least 12 hours, more preferably for at least 16 hours, more preferably for at least 20 hours, more preferably for at least 24 hours.

Preferably, step a) in the BINAP process of the present invention comprises introducing lithium metal to a solution of a bidentate, rotationally hindered diphenylphosphine-containing ligand in a non-reactive solvent.

Preferably, step a) in the BINAP process of the present invention comprises forming a mixture of lithium metal and a first non-reactive solvent, and combining this mixture with a solution of a bidentate, rotationally hindered diphenylphosphine-containing ligand (such as a ligand having formula (I)) in a second non-reactive solvent, wherein the first and second non-reactive solvents may be the same or different.

Step b) of the process of the BINAP present invention comprises reacting the metallated product with an electrophile or a transition metal complex. Typically, this reagent is brought into contact with the metallated product in the form of a solution in a non-reactive solvent, which may be the same or different to the non-reactive solvent(s) used in step a). However, some electrophiles such as methyl iodide are themselves liquids. Such electrophiles can optionally be added as neat compounds (i.e. not in the form of a solution with a non-reactive solvent). However, care must be taken to ensure that the reaction between the metallated product and the electrophile or transition metal complex does not happen too rapidly. Not only is this potentially dangerous, but if excess heat is generated the atropisomer may obtain enough energy to allow rotation around the rotationally hindered bond. Therefore, it is preferred to introduce the electrophile in the form of a solution in a second non-reactive solvent, particularly if the product of step a) is not sufficiently dilute.

As noted above, if sufficient heat is generated during the reaction, the atropisomer may obtain enough energy to allow rotation around the rotationally hindered bond. As such, the reaction mixture in step a) and/or step b) may optionally be cooled, for example with a cooling means. Suitable cooling means would be familiar to the skilled person, and include ice baths, dry ice (optionally dissolved in a solvent such as isopropyl alcohol) and the like.

After reaction with the electrophile, it is preferred to work up the reaction, for example to remove any unreacted metallated ligand and/or lithium metal. As the skilled person would understand, some types of electrophile such as alkenes also require a work up step to protonate the adduct formed from the metallated phosphine and the electrophile. The skilled person would be familiar with what types of reactions would require a work up step, and how to carry out such steps.

The bidentate, rotationally hindered diphenylphosphine-containing ligand used in the BINAP process of the invention is preferably selected from BINAP, TolBINAP, H$_8$-BINAP, BINAPO, QUINAP, PINAP, PHOX, PINPHOS, BIPHEMP, MOP, MAP, Gilbertson phosphinooxazoline, VALAP, iminophosphine, C3-TunePhos, BINAPHOS, MeOBIPHEP, (4-NMe$_2$)-MeOBIPHEP, p-Tol-MeOBIPHEP, and SEGPHOS.

Preferred ligands used in the BINAP process of the present invention are selected from BINAP, TolBINAP, H$_8$-BINAP, QUINAP, PINAP, PHOX, PINPHOS, BIPHEMP, MOP, MAP, VALAP, C3-TunePhos, BINAPHOS, MeOBIPHEP, (4-NMe$_2$)-MeOBIPHEP, p-Tol-MeOBIPHEP, and SEGPHOS.

Preferably, the ligand used in the BINAP process of the present invention contains at least one PPh$_2$ moiety. More preferably, the ligand used in the MAP process of the present invention contains two PPh$_2$ moieties.

The skilled person would recognise that the BINAP reactions described above may require more careful control of the reaction conditions, such as the use of distilled and degassed solvents, argon atmosphere and glovebox techniques.

The compounds of formula (II), Op and (IV) are active as catalysts. Typical reactions in which gold complexes are known to catalyse have been summarised in Chem. Rev., 2008, 108, pp 3239-3265; Chem. Rev., 2008, 108, pp 3266-3325; and Chem. Soc. Rev., 2009, 38, pp 3208-3221. The catalysts of the present invention are believed to be active in the reactions summarised in these review articles, which would be familiar to the skilled person. The compound of formula (II), (Ill) and (IV) are capable of acting as stereoselective catalysts, due to the presence of the chiral centre in the G substituent.

The compounds of formula (II), (HI) and (IV) are found to be particularly useful in reactions that involve activation, of a π-system to nucleophilic attack, preferably nucleophilic attack by alcohols, water, amines, thiols and halogens.

Thus, the present invention also relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) as a catalyst, preferably a stereoselective catalyst.

Preferably, the present invention relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) in the activation of a π-system to nucleophilic attack, preferably nucleophilic attack by an alcohol, water, an amine, a thiol or a halogen.

Preferably, the present invention relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) in an addition reaction of compound to a π-system, preferably a hydration reaction of a π-system.

In the above described reactions, the π-system is preferably a carbon-carbon double bond or a carbon-carbon triple bond, particularly preferably a carbon-carbon double bond.

The above described reactions can involve to separate molecules, or alternatively may be an reaction of a π-system with an internal nucleophile such as a cyclisation reaction. These internal reactions can be "cascade" reactions, wherein two or more consecutive reactions involving different π-systems in the same molecule, typically to form a multi-ring system.

Thus, the present invention preferably relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) as a catalyst in a cyclisation reaction.

Preferably, the present invention relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) as a catalyst for a Rautenstrauch rearrangement.

Preferably, the present invention relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) as a catalyst for a Claisen rearrangement, or a derivative reaction thereof.

Preferably, the present invention relates to the use of a compound of formula (II), (IIa), (IIb), (IIc), (IId), (III), (IIIa), (IIIb), (IIIc), (IIId), (IIIe), (IIIf), (IIIg), (IVa), (IVb) or (IVc) as a catalyst for a Schmidt reaction.

Preferably, the present invention relates to the use of a compound of formula (II), (IIa), (IIb), (IIc), (IId), (III), (IIIa), (IIIb), (IIIc), ((IId), (IIIe), (IIIf), (IIIg), (IVa), (IVb) or (IVc) as a catalyst for a rind forming reaction.

Preferably, the ring forming reaction is a cyclisation.

Preferably, the ring forming reaction is a cyclopropanation.

Preferably, the ring forming reaction forms a 3-7 membered ring bearing one or more heteroatoms; preferably a furan or a hydrogenated alternative thereof; a pyrrole, a pyrroline or a pyrrolidene; or a thiophene.

Preferably, the present invention relates to the use of a compound of formula (II), (IIa), (IIb), (IIc), (IId), (III), (IIIa), (IIIb), (IIIc), ((IId), (IIIe), (IIIf), (IIIg), (IVa), (IVb) or (IVc) as a catalyst for a cascade reaction.

The skilled person would recognise that the presence of water in the catalytic medium may lead to dissociation of the ligand and hence a reduction or complete loss of catalytic activity. The catalytic reactions of the present invention are therefore preferably carried out in an essentially water-free medium. Preferably, the medium used in the reaction of the present application is water-free.

A typical reaction that can be performed using the compounds of the invention include the formation of a hexahydroanthracen-1-ol, such as the reaction reported by Michelet et al., Org. Lett. 2009, 11, 2888. The general reaction is as shown below:

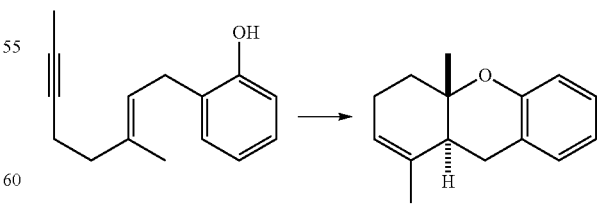

A further reaction that can be performed by the catalysts of the present invention is the 5-exo-dig ring formation shown below. The reaction has previously been reported for other Au(I) catalysts by Toste, D et. al. J. Am. Chem. Soc. 2004, 126, 4526.

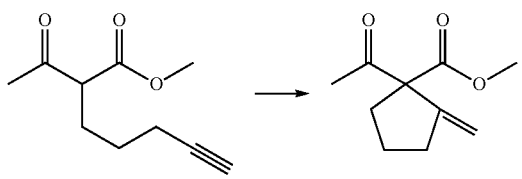

SYNTHETIC EXAMPLES

All reagents and solvents were used without further purification from commercially available sources unless otherwise stated. Dry diethyl ether and tetrahydrofuran were distilled from sodium/benzophenone under an atmosphere of nitrogen. Dichloromethane, toluene, triethylamine, and diisopropylamine were distilled from calcium hydride under atmosphere of nitrogen. Under anhydrous conditions, all apparatus was flame-dried before either cooling in sealed dessicator containing silica gel, cooling under vacuum (0.3 mmHg) or under a continuous flow of nitrogen or argon. Evaporation under reduced pressure was performed on a Buchi rotary evaporator, using a diaphragm vacuum pump. Reduced pressure was achieved by using a Leybold static oil pump (0.05 mmHg) unless otherwise stated. The IR spectra were recorded on spectrometer Perkin Elmer FT-IR Spectrum One equipped with a diamond top plate. Mass spectra were obtained by using VG Autospec Magnetic Sector MS and Bruker Daltonic FT-ICR-MS Ape III instruments, using electron impact (EI) or fast atom bombardment (FAB). The $^1$H nuclear magnetic resonance spectra were recorded on a Varian 400 (400 MHz) or Varian 500 (500 MHz). Chemical shifts are reported in parts per million (ppm) relative to residual CHCl$_3$ (δ 7.26 ppm), H$_2$O (δ 4.80 ppm), DMSO (δ 2.50 ppm), CH$_3$OH (δ 4.87 ppm). The following abbreviations are used to describe the multiplicity of given signals: s=singlet, d=doublet, t=triplet, q=quartet, quin=quintet, sex=sextet, sept=septet, m=multiplet and br=broad. Coupling constants, J, are given wherever appropriate in Hertz. The $^{13}$C nuclear magnetic resonance spectra were recorded on a Varian 500 (126 MHz). Chemical shifts are reported in parts per million (ppm) relative to CDCl$_3$ (central line of triplet δ 77.00 ppm), DMSO (central line of septet δ 39.51 ppm), CD$_3$OD (δ 49.15 ppm). The following abbreviations are used to describe the multiplicity of given signals: C=quaternary, CH=methane, CH$_2$=methylene, CH$_3$=methyl. Coupling constants, J, are given wherever appropriate in Hertz. The $^{31}$P nuclear magnetic resonance spectra were recorded on a Varian 400 (162 MHz) referenced to 85% phosphoric acid in water. The $^{19}$F nuclear magnetic resonance spectra were recorded on a Varian 400 (376 MHz). All reactions were monitored, where appropriate, by T.L.C. using Macherey-Nagel plates with a 0.2 mm layer of 60 F$_{254}$ silica gel containing a fluorescent indicator. Visualization was achieved with U.V. light (254 mm) followed by an ethanolic solution of phosphomolibdic acid. Flash column chromatography was carried out using Apollo Zeoprep 60 Hyd 35-70 micron silica gel. Petroleum ether (PET) usually refers to the fraction distilled narrow alkene hydrocarbons distillate fraction from crude oil in the 40 to 60° C. range, unless otherwise stated, and was distilled prior to use.

Synthesis Example 1

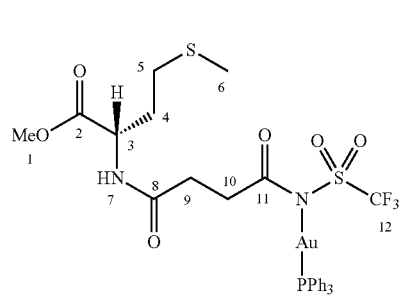

Synthesis Example 1a

L-Methionine methyl ester hydrochloride (2)

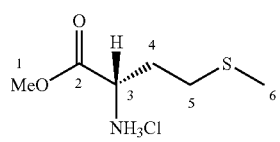

L-Methionine (0.5 g, 1 equivalent) was suspended in methanol (30 ml C=0.1M) in a 100 ml flask equipped with a magnetic stirrer and placed under nitrogen. Thionyl chloride (0.5 ml, 2 equivalents) was added to the solution dropwise at 0° C. then heated under reflux for 16 hours. The reaction mixture was then evaporated to yield a pale yellow solid. The solid was triturated with hot diethyl ether and the solution discarded to leave the title compound 2' a white solid which was further dried under vacuum. (0.65561 g, 98% yield).

$^1$H NMR (D$_2$O, 500 MHz) δ$_H$: 4.24 (1H, m, 3) 3.79 (3H, s, 1), 2.63 (2H, t, 5), 2.25 (1H, m, 4), 2.16 (1H, m, 4), 2.06 (1H, s, 6)

$^{13}$C NMR (D$_2$O, 125 MHz) δ$_c$: 170.58 (2), 53.64 (1), 51.70 (3), 28.71 (4), 28.41 (5), 13.85 (6).

IR (neat, v$_{max}$, cm$^{-1}$): 2880.8/2676.2 (CH$_3$, CH$_2$, CH), 2016.2, 1742.2 (C=O, ester), 1483.6, 1443.5, 1227+1194.7+1149.8+1079.5 (C—O).

HRMS m/z (+ESI): C$_6$H$_{14}$NO$_2$S, mass found=164.074 (Error=0.071 ppm)

Synthesis Example 1b (S)-4-((1-methoxy-4-(methylthio)-1-oxobutan-2-yl)amino)-4-oxobutanoic acid (3)

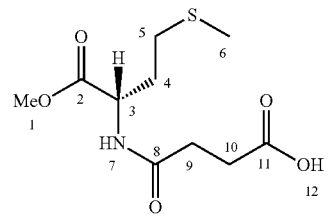

Compound 2 (0.25 g, 1 eq.) was suspended in CH$_2$Cl$_2$ (12.5 ml, C=0.1M). Triethylamine (0.26 ml, 1.5 eq.) was added to the solution which was then stirred for 10 minutes. After stirring 4-dimethylamino pyridine (0.015 g, 0.1 eq.) and succinic anhydride (0.125 g, 1 eq.) were added and the reaction left to stir for 16 hours at room temperature. The reaction mixture was then shaken with 3×20 ml portions of hydrochloric acid (2M), the aqueous washings were subsequently extracted with 3×20 ml portions of diethyl ether. The DCM portion was discarded and the ether layers were combined and dried over anhydrous MgSO$_4$, filtered and evaporated to yield a white solid 3 (0.199 g, 60% yield).

$^1$H NMR (CDCl$_3$, 500 MHz) δ$_H$: 10.6 (1H, s, 12) 6.71 (1H, d, 7), 4.69 (1H, dd, 3), 3.73 (3H, s, 1), 2.68 (2H, m, 9), 2.54 (2H, t, 10), 2.49 (2H, t, 5), 2.13 (1H, m, 4), 2.10 (3H, s, 6), 1.96 (1H, m, 4).

$^{13}$C NMR (CDCl$_3$, 125 MHz) δ$_c$: 176.9 (11), 172.53 (2), 171.88 (8), 52.79 (1), 51.64 (3), 31.54 (4), 30.54 (10), 29.86 (5), 29.30 (9), 15.35 (6).

IR (neat, $v_{max}$, cm$^{-1}$): 3309.2+3104.6 (O—H, acid), 2923.2, 1746 (C=O, ester), 1715.2 (C=O, acid), 1651 (C=O, amide), 1533.4, 1410.1, 1227+1204+1174+1159 (C—O).

HRMS m/z (+ESI): C$_{10}$H$_{17}$NNaO$_5$S, mass found 286.0720 (Error=1.96 ppm).

Synthesis Example 1c (S)-methyl 4-(methylthio)-2-(4-oxo-4-(trifluoromethylsulfonamido)butanamidOlbutanoate (4)

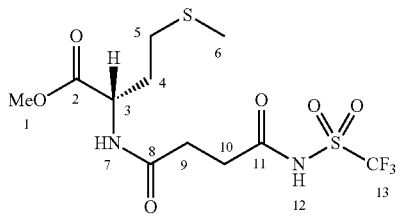

Compound 3 (0.53 g, 1 eq.) and triflic amide (0.3 g, 1 eq.) were dissolved in CH$_2$Cl$_2$ (7.5 ml, C=0.38M) and cooled to 0° C. EDC (0.36 ml, 1.025 eq.) was then added and the reaction mixture stirred at 0° C. for 15 minutes after which it was warmed to room temperature and left to stir for 48 hours. The reaction mixture was then evaporated and taken up in ethyl acetate (10 ml) and washed with citric acid, sodium hydrogen carbonate and brine (10 ml portions). The combined aqueous washings were then extracted with diethyl ether using continuous extraction equipment for 18 hours. The diethyl ether solution was dried over anhydrous MgSO$_4$, filtered and evaporated to yield a yellow oil. The crude oil was purified by column chromatography using a gradient solvent system of 0-5% methanol in diethyl ether to isolate the product 4 as a pale yellow oil (baseline spot, 0.1788 g, 22.5% yield).

$^1$H NMR (CDCl$_3$, 500 MHz) δ$_H$: 6.83 (1H, d, 7), 4.74 (1H, dd, 3), 3.78 (3H, s, 1), 2.82 (2H, m, 10), 2.71 (2H, t, 9), 2.51 (2H, t, 5), 2.17 (1H, m, 4), 2.10 (3H, s, 6), 2.03 (1H, m, 4).

$^{13}$C NMR (CDCl$_3$, 125 MHz) δ$_c$: 172.37 (2), 171.88 (8), 169.35 (11), 52.79 (1), 52.03 (3), 32.16 (10), 31.05 (4), 29.79 (5), 29.70 (9), 15.39 (6).

IR (neat, $v_{max}$, cm$^{-1}$): 3371, 2919.4, 1734.5 (C=O, amide), 1649.6, 1537.7, 1441.2, 1387.2, 1201.6+1134.8+1096.8 (C-O).

HRMS m/z (+ESI): C$_{11}$H$_{18}$F$_3$N$_2$O$_6$S$_2$, mass found=395.0553 (Error=2.19 ppm)

Synthesis Example 1d

Compound (1)

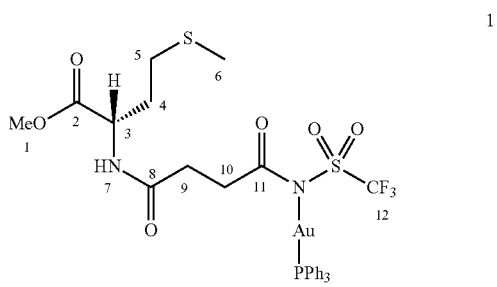

Compound 4 (0.0489 g, 1 eq.) was dissolved in dry CH$_2$Cl$_2$ (2.5 ml C=0.05M). Ag$_2$CO$_3$ (0.034 g, 1 eq.) was added, the reaction flask covered with paper and then stirred for 5 minutes. Triphenylphosphine gold chloride (0.061 g, 1 eq.) was then added and the reaction mixture placed under an atmosphere of nitrogen. The reaction stirred for 1.5 hours. The reaction mixture was diluted with CH$_2$Cl$_2$ (10 ml), filtered using a Pasteur pipette and cotton wool and then evaporated to isolate a light brown oil 1 (0.0903 g, 85% crude yield).

$^1$H NMR (CDCl$_3$, 500 MHz) δ$_H$: 7.57-7.45 (15H, m, aromatics 13), 6.49 (1H, d, 7), 4.7 (1H, m, 3), 3.72 (3H, s, 1), 3.1 (2H, m, 10), 2.56 (4H, m, 9 and 5), 2.16 (1H, m, 4), 2.08 (3H, s, 6), 1.98 (1H, m, 4).

$^{13}$C NMR (CDCl$_3$, 125 MHz) δ$_c$: 177.35 (11), 172.24 (2), 171.67 (8), 134.19 (13), 134.07(13), 132.14 (13), 132.12 (13), 129.41 (13), 129.31 (13), 52.41 (1), 51.52 (3), 33.88 (10), 31.77 (4), 31.27 (9), 30.20 (5), 15.75 (6)

$^{31}$P NMR (CDCl$_3$, 161.72 Mhz) δ$_p$: 30.5 (13), 29.0 (residual triphenylphosphineoxide present in the purchased gold starting material).

HRMS m/z (+ESI): C$_{29}$H$_{31}$AuF$_3$N$_2$NaO$_6$PS$_2$, mass found=875.0871 (Error=5.89 ppm)

Synthesis Example 2

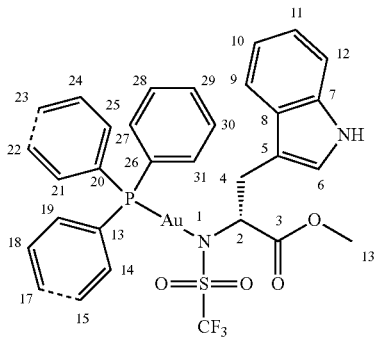

Synthesis Example 2a (2R)-3-(1H-indol-3-yl)-1-methoxy-1-oxopropan-2-aminium chloride Thionyl chloride (9.87 mmol, 0.72 mL) was added dropwise to a solution of D-tryptophan (1.000 g, 4.89 mmol) in methanol (33 mL). The reaction was heated to reflux with vigorous stirring for 24 h. After cooling, the reaction mixture was concentrated under reduced pressure and residual methanol traces removed by azeotropic distillation with dichloromethane (10 mL) under reduced pressure to give the title compound as a white solid (1.070 g, 86%).

$^1$H NMR (500 MHz, D$_2$O) δ=7.52 (1H, d, J=7.9, 9-H), 7.46 (1H, d, J=8.1, 12-H), 7.26-7.10 (3H, m, 4, 5, 9-H), 4.37 (1H, t, J=6.0, 2-H), 3.73 (3H, s, β-H), 3.44-3.31 (2H, m, 4-H).

$^{13}$C NMR (126 MHz, D$_2$O) δ=170.4 (2-C), 136.3 (7-C), 126.4 (8-C), 125.4 (6-C), 122.3 (11-CH), 119.6 (10-CH), 118.1 (9-CH), 112.1 (12-CH), 106.0 (5-C), 53.6 (13-CH$_3$), 53.3 (2-CH), 25.7 (4-CH$_2$).

IR (diamond, v$_{MAX}$, cm$^{-1}$) 3261 (NH st), 2870 (N$^+$—H st), 2023 (Ar comb), 1748 (C=O st), 1229, 1211 (CO—O st as), 1181 (C—O st as).

Acc. Mass (FAB): C$_{12}$H$_{15}$N$_2$O$_2$ Found: 219.1120 m/z Calculated: 219.1128 m/z.

Synthesis Example 2b

Methyl N-[(trifluoromethyl)sulfonyl]-D-tryptophanate (6a)

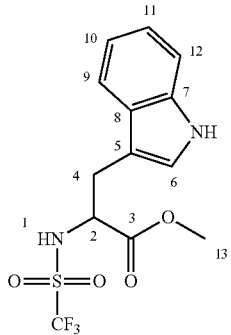

6a

A solution of triflic anhydride (1.3816 g, 4.887.10$^{-3}$ mol) in DCM (4.897 ml) was dripped into a solution of tryptophan methoxy ether ester (1.0737 g, 4.897.10$^0$ mol) and Et$_3$N (1.4866 g, 0.01469 mol) in DCM (18.9 ml) at −78° C. The mixture was stirred for 24 h at room temperature. Water was added and the pH was adjusted to 5 with conc. HCl, then extracted with diethyl ether, dried over MgSO$_4$, filtered and concentrated. Purification by column chromatography (diethyl ether) afforded the title compound 6a as brown-yellow solid (1.5478 g, 90%).

$^1$H NMR (500 MHz, CDCl$_3$) δ 8.17 (s, 1H, N-1), 7.52 (d, J=7.9, 1H, 9-H), 7.37 (d, J=8.1, 1 H, 12-H), 7.24-7.19 (m, 1H, 10-H), 7.17-7.12 (m, 1H, 11-H), 7.04 (d, J=2.3, 1H, 6-H), 4.57 (t, J=5.0, 1H, 2-H), 3.71 (s, 3H, 13-H), 3.38 (ddd, J=4.9, 14.8, 20.3, 2H)

$^{13}$C NMR (126 MHz, CDCl$_3$) δ 170.67 (3-C), 136.17 (7-C), 127.12 (8-C), 125.13 (14-CF), 124.58 (14-CF), 123.46 (6-CH), 123.28 (14-CF), 122.53 (11-CH), 120.72 (14-CF), 120.00 (10-CH), 118.29 (9-CH), 118.17 (14-CF), 111.42 (12-CH), 107.97 (5-C), 57.39 (2-CH), 52.98 (13-CH$_3$), 29.34 (4-CH$_2$).

IR (diamond, v$_{max}$, cm$^{-1}$) 3402.90 (ar NH st), 3261.49 (NH st), 2197.01, 2157.16, 1031.43 (Ar comb), 1712.56 (C=O st), 1230.60 (CO—O st), 1185.04 (S—O st as), 1145.47 (S—O st sy)

HRMS: C$_{13}$H$_{13}$F$_3$N$_2$O$_4$SNa

Found: 373.0440 m/z Err[ppm]: −1.47

Using similar methodology, equivalent compounds were synthesised using the following amino acid base materials:

| Compound | Amino Acid Side Chain | Yield |
|---|---|---|
| 6b | CH$_2$CH$_3$ | 85% |
| 6c | CH$_2$CH(CH$_3$)$_2$ | 77% |
| 6d | CH(CH$_3$)$_2$ | 72% |
| 6e | 4-hydroxyphenylmethylene | 65% |

Synthesis Example 2c

Compound 5a

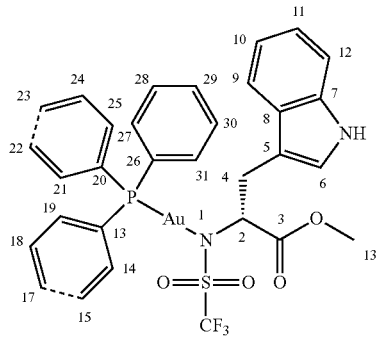

5a

To the solution of 6a (0.050 g, 1.4273.10$^4$ mol) in DCM (3.57 ml), Ag$_2$CO$_3$ (0.0386 g, 1.4273.10$^{-4}$ mol) was added and stirred for 5 min. The solution of Ph$_3$PAuCl (0.0706 g, 1.4273.10$^{-4}$ mol) was added to the solution of V03 MB44A and Ag$_2$CO$_3$ and stirred for 1.5 h. Filtration with Celite and evaporation were followed. The title compound appeared as pale yellow solid (0.1146 g, 99%).

$^1$H NMR (500 MHz, CDCl$_3$) δ 7.58-6.97 (m, 20H, Ar), 5.06 (q, J=6.1, 1H, 2-H), 3.65 (s, 3H, 13-H), 3.39 (ddd, J=5.7, 14.7, 21.2, 2H, 4-H).

$^{13}$C NMR (126 MHz, CDCl$_3$) δ 174.06 (3-C), 135.88 (7-C), 134.21 (Ar), 134.10 (Ar), 131.70 (Ar), 131.68 (Ar), 129.11 (Ar), 129.01 (Ar), 128.57 (Ar), 127.78 (8-CH), 123.72 (6-CH), 122.03 (11-CH), 119.40 (10-CH), 118.95 (9-CH), 111.12 (12-CH), 110.47 (5-C), 60.84 (2-CH), 52.04 (13-CH$_3$), 31.66 (4-CH).

IR (diamond, v$_{max}$, cm$^{311}$) 3398.31 (ar NH st), 2180.22 (Ar comb), 1738.17 (C=O st), 1212.30 (CO—O st), 1176.52 (S—O st as), 1100.59 (S—O st sy)

HRMS: C$_{31}$H$_{27}$AuF$_3$N$_2$O$_4$PSNa

Found: 831.0939 m/z Err[ppm]: −0.56

Using similar methodology, equivalent compounds were synthesised using the following amino acid base materials:

| Compound | Amino Acid Side Chain | Yield |
|---|---|---|
| 5b | CH$_2$CH$_3$ | 100% |
| 5c | CH$_2$CH(CH$_3$)$_2$ | 97% |
| 5d | CH(CH$_3$)$_2$ | 91% |
| 5e | 4-hydroxyphenylmethylene* | 100% |

*NB - Compound 5e contains a triflate group on the tyrosine hydroxy group, which is included when functionalising the nitrogen atom of the amino acid. The full synthesis for compound 5e is as follows:

(2S)-3-(4-hydroxyphenyl)-1-methoxy-1-oxopropan-2-aminium chloride

Thionyl chloride (6.62 mmol, 0.48 mL) was added dropwise to a solution of L-tyrosine (0.600 g, 3.31 mmol) in methanol (22 mL). The reaction was heated to reflux with vigorous stirring for 24 h. After cooling, the reaction mixture was concentrated under reduced pressure and the residual methanol removed by azeotropic distillation with dichloromethane (10 mL) under reduced pressure to give the title compound as a white solid (0.646 g, 84%).

$^1$H NMR (500 MHz, D$_2$O) δ=7.08 (2H, d, J=7.7, 6, 7-H), 6.83 (2H, d, J=7.7, 8, 9-H), 4.31 (1H, t, J=5.9, 2-H), 3.76 (3H, s, 11-H), 3.24-3.02 (2H, m, 4-H).

$^{13}$C NMR (126 MHz, D$_2$O) δ=170.1 (2-C), 155.2 (10-C), 130.8 (6,7-CH), 125.4 (5-C), 116.0 (8,9-CH), 54.2 (2-CH), 53.5 (11-CH$_3$), 34.8 (4-CH$_2$).

IR (diamond, v$_{max}$, cm$^{-1}$) 3335 (NH st), 2877 (N$^+$—H st), 1983 (Ar comb), 1741 (C=O st), 1225 (CO—O st as), 1199 (C—O st as).

Acc. Mass (FAB): C$_{10}$H$_{14}$NO$_3$ Found: 196.0962 m/z Calculated: 196.0968 m/z.

(S)-methyl 3-(4-(((trifluoromethyl)sulfonyl)oxy)phenyl)-2-(trifluoromethylsulfonamido)propanoate A solution of triflic anhydride (0.934 g, 3.3.1 mmol) in dichloromethane (3.31 mL) was added dropwise to a solution of (2S)-3-(4-hydroxyphenyl)-1-methoxy-1-oxopropan-2-aminium chloride (0.767 g, 3.31 mmol) and triethylamine (1.005 g, 9.93 mmol) in dichloromethane (12.79 mL) at −78° C. The mixture was stirred for 24 h at room temperature. Water (5 mL) was added and the pH was adjusted to pH=5 using 32% hydrochloric acid. The aqueous layer was extracted with diethyl ether. The organics extracts were combined, dried over anhydrous magnesium sulfate, filtered and concentrated under reduced pressure. Purification by column chromatography (diethyl ether) afforded the title compound as yellow solid (0.704 g, 49%).

$^1$H NMR (500 MHz, CDCl$_3$) δ=7.29-7.22 (4H, m, 6, 7, 8, 9-H), 4.49 (1H, t, J=6.0, 1H, 2-H), 3.78 (3H, s, 11-H), 3.23-3.13 (2H, m, 4-H).

$^{13}$C NMR (126 MHz, CDCl$_3$) δ=170.4 (3-C), 149.2 (10-C), 134.8 (5-C), 131.3 (6, 7-CH), 123.1 (12-CF), 121.8 (8,9-CH), 120.6 (12-CF), 120.0 (12-CF), 118.0 (12-CF), 117.4 (12-CF), 115.8 (12-CF), 57.7 (2-CH), 53.2 (11-CH$_3$), 38.9 (4-CH$_2$).

IR (diamond, v$_{max}$, cm$^{-1}$) 3349 (O—H st), 3221 (NH st), 2176 (Ar comb), 1724 (C=O st), 1238 (CO—O st), 1199 (S—O st as), 1141 (S—O st sy).

Acc. Mass (FAB): C$_{14}$H$_{10}$F$_6$NO$_7$S$_2$ Found: 481.9778 m/z Calculated: 481.9797 m/z.

Compound 5e

Silver carbonate (42.1 mg, 0.153 mmol) was added to a solution of the ligand (50 mg, 0.153 mmol) in dichloromethane (3.82 mL) and stirred for 5 min. A solution of triphenylphosphine gold chloride (75.6 mg, 0.153 mmol) was added and stirred for 1.5 h. The reaction mixture was filtered through Celite and the solvent concentrated under reduced pressure to give the corresponding compound as white solid (1.548 g, 90%).

$^1$H NMR (500 MHz, CDCl$_3$) δ=7.52-7.44 (15H, m, Ar), 7.27 (2H, d, J=9.6, 6, 7-H), 7.00 (2H, d, J=8.6, 2H, 8, 9-H), 4.91 (1H, m, 2-H), 3.67 (3H, s, 11-H), 3.26-3.16 (2H, m, 4-H).

$^{13}$C NMR (126 MHz, CDCl$_3$) δ=170.8 (3-C), 148.4 (10-Ar), 137.0 (5-Ar), 134.2 (Ar), 134.1 (Ar), 132.01 (Ar), 131.5 (6,7-Ar), 129.3 (Ar), 129.2 (Ar), 121.0 (8,9-Ar), 61.5 (2-CH), 52.0 (11-CH$_3$), 41.7 (4-CH$_2$).

$^{31}$P NMR (162 MHz, CDCl$_3$) δ=31.30 (s).

IR (diamond, v$_{max}$, cm$^{-1}$) 2956 (O—H st), 2073 (Ar comb), 1738 (C=O st), 1249 (CO—O st), 1176 (S—O st as), 1137 (S—O st sy).

Ace. Mass (FAB): C$_{30}$H$_{25}$AuF$_6$NO$_7$PS$_2$ Found: 940.0383 m/z Calculated: 940.0272 m/z, Synthesis Example 3

Compound 7

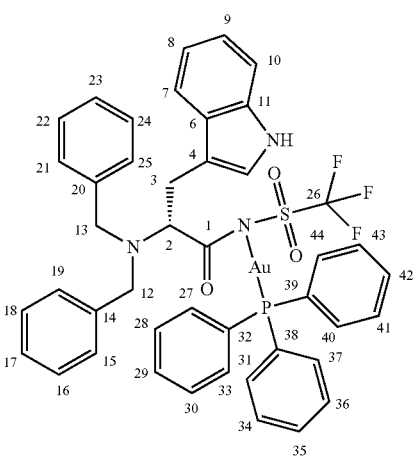

7

Synthesis Example 3a

N,N-dibenzyl-N[(trifluoromethyl)sulfonyl]-D-tryptophanamide (8)

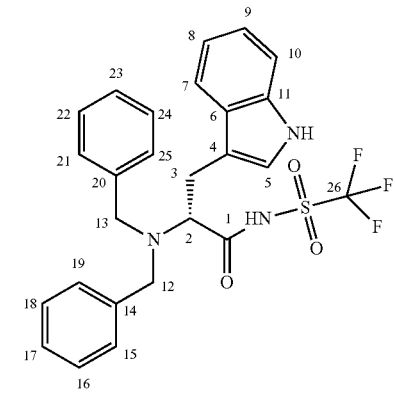

8

N,N-dibenzyl-D-tryptophan (0.152 g, 3.9535*10$^{-4}$ mol), Triflic amine (0.0589 g, 3.9535*10$^{-4}$ mol) and HOBt*H$_2$O (0.0605 g, 3.9535*10$^{-4}$ mol) were dissolved in CH$_2$Cl$_2$ and cooled to 0° C. EDC (0.060 g, 3.8632*10$^{-4}$) was added and mixture was stirred for 15 min at 0° C. and at RT during 3 days. The precipitate was filtered off and solvent was evaporated. The residue was dissolved in 5 ml of AcOEt and washed with 1M citric acid, saturated NaHCO$_3$, brine, dried over anhydrous MgSO$_4$ and concentrated under reduced pressure. Purification by column chromatography (diethyl ether) afforded the title compound 8 as white solid (0.1491 g, 73%).

$^1$H NMR (500 MHz, CDCl$_3$) δ 7.37-6.82 (m, 15H, Ar), 4.09-3.53 (m, 6H, 12, 13, 3(1H)—CH$_2$ 2-CH), 3.07 (m, 1H, 3-CH$_2$).

IR (diamond, $v_{max}$, cm$^{-1}$) 3403.21 (ar NH st), 2919.69 (NH st), 2019.56 (Ar comb), 1619.39 (C=O st amide), 1179.12, 1180.95 (S—O st as), 1125.62 (S—O st sy)

HRMS: $C_{26}H_{24}F_3N_3O_3SNa$

Found: 538.1383 m/z Err[ppm]: −2.84

Synthesis Example 3b

Compound 7

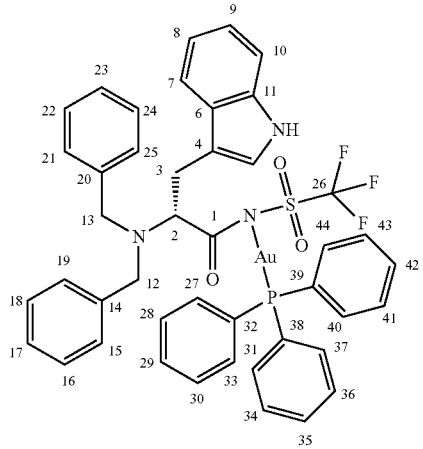

To the cooled mixture at 0° C. of 8 (0.1144 g, 2.2190*10$^{-4}$ mol) in CH$_2$Cl$_2$ (C=0.1M, 2.52 ml) Ag$_2$CO$_3$ (0.1101 g, 3.99424*10$^{-4}$ mol) was added and stirred 5 min, followed addition of Ph$_3$PAuCl (0.1101 g, 2.2190*10$^{-4}$ mol) and stirred 2 days at 0° C. Mixture was filtered off and concentrated under reduced pressure. (0.2136 g, 99%).

$^{31}$P NMR (162 MHz, CDCl$_3$) δ 33.00 (s, 13), 29.92 (s, 142), 28.97 (s, 1).

$^1$H NMR (500 MHz, CDCl$_3$) δ 7.61-6.67 (m, 36H), 4.26 (s, 1H), 4.16 (d, J=14.3, 2H), 3.80 (d, J=14.3, 2H), 3.60-3.53 (m, 1H), 3.12 (dd, J=4.5, 14.1, 1H).

Synthesis Example 4

Compound 9a

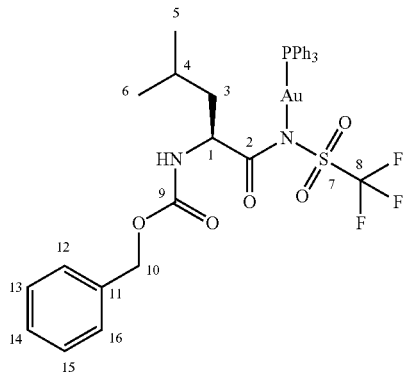

Synthesis Example 4a N-benzoxycarbonyl-L-leucine (10a)

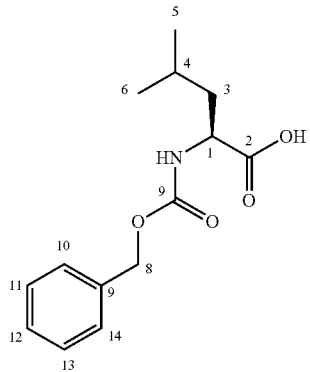

To the solution of L-leucine (0.400 g, 3.049*10$^{-3}$ mol) in 2M NaOH aq. (3.75 ml) cooled to 0° C., benzyl chloroformate (3.5374*10$^{-3}$ mol, 0.52 ml) was added dropwise over 15 min. The mixture was stirred at RT for another 2 h, and then acidified with HCl conc. The aqueous layer was extracted with AcOEt (3×10 ml) and the combined organic layers were dried over anhydrous magnesium sulfate. The solvent was evaporated in vacuo to give crude N-benzoxycarbonyl-L-leucine. (colourless oil) (76%).

Colourless oil, Data J. Frelek at al Tetrahedron Asymmetry 2006, 17, 2469.

Synthesis Example 4b

N$^2$-[(benzyloxy)carbonyl]-N$^1$-[(trifluoromethyl)sulfonyl]-L-leucinamide (11a)

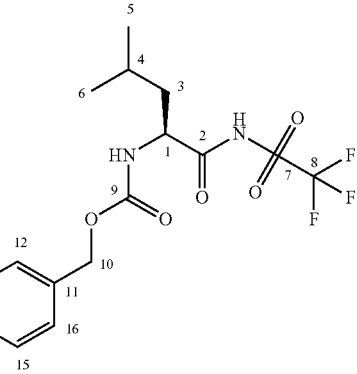

N-benzoxycarbonyl-L-leucine (0.100 g, 3.769*10$^4$ mol), Triflic amine (0.0562 g, 3.769*10$^{-4}$ mol) and HOBt*H$_2$O (0.0577 g, 3.769*10$^{-4}$ mol) were dissolved in CH$_2$Cl$_2$ and cooled to 0° C. EDC (0.060 g, 3.8632*10$^{-4}$ mol) was added and mixture was stirred for 15 min at 0° C. and at RT during 3 days. The precipitate was filtered off and solvent was evaporated. The residue was dissolved in 5 ml of AcOEt and washed with 1M citric acid, saturated NaHCO$_3$, brine, dried over anhydrous MgSO$_4$ and concentrated under reduced pressure. Purification by column chromatography (diethyl ether) afforded the title compound as white solid (0.0794 g, 53%).

$^1$H NMR (500 MHz, CDCl$_3$) δ 7.33-7.16 (m, J=7.2, 5H), 5.56 (s, 1H), 5.25-4.80 (m, J=82.0, 2H), 4.06 (s, 1H), 1.63-1.32 (m, J=88.5, 3H), 0.81 (s, 6H).

$^{13}$C NMR (126 MHz, CDCl$_3$) δ 181.74 (2-C), 157.32 (9-C)), 135.77 (11-C(Ar)), 128.44 (12,14,16-CH(Ar)), 128.12 (8-CF$_3$), 127.82 (13,15-CH(Ar)), 67.27 (10-CH$_2$), 56.80 (1-CH), 40.75 (3-CH$_2$), 24.57 (4-CH), 22.69 (6-CH$_3$), 21.62 (5-CH$_3$).

IR (diamond, v$_{max}$, cm$^{-1}$) 3393.33 (NH st), 2019.56 (Ar comb), 1703.90, 1621.68 (C=O st amide), 1292.92 (CO—O st), 1180.95 (S—O st as), 1124.20 (S—O st sy)

HRMS: C$_{15}$H$_{19}$F$_3$N$_2$O$_5$SNa

Found: 419.0859 mfz Err[ppm]: −0.26

Using similar methodology, equivalent compounds were synthesised using the following amino acid base materials:

| Compound | Amino Acid Side Chain | Yield |
|---|---|---|
| 11b | CH(CH$_3$)$_2$ | 76% |

Synthesis Example 4c

Compound 9a

To the cooled mixture at 0° C. of the ligand 11a (0.100 g, 0.252 mmol) in CH$_2$Cl$_2$ (0.1 M, 2.52 ml), Ag$_2$CO$_3$ (0.1260 g, 4.5694*10$^{-4}$ mol) was added and stirred 5 min, followed by the addition of Ph$_3$PAuCl (0.125 g, 0.252 mmol) and stirred 2 days at 0° C. The mixture was then filtered and the resulting solution concentrated under reduced pressure.

Synthesis Example 5

Compound 12

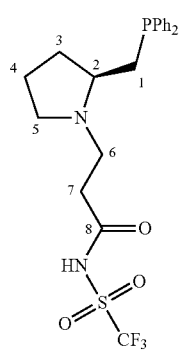

12

Synthesis Example 5a methyl 3-{(2S)-2[(diphenylphosphino)methyl]pyrrolidin-1-yl}propanoate (13)

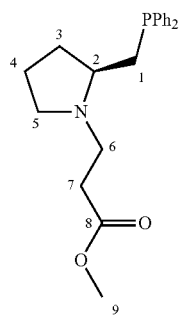

13

(2S)-2-[(diphenylphosphino)methyl]pyrrolidine (shown below) was prepared following the procedure of Tomiaka *Tetrahedron. Lett.* 1996. 37. 7805

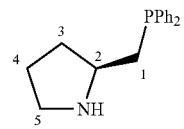

A solution of methyl-3-bromopropionate (1.55 g, 9.28 mmol, 1.01 ml) in dichloromethane (8.0 ml) was added dropwise to a solution of the triethylamine (1.88 g, 18.57 mmol, 2.61 ml) and (2S)-2-[(diphenylphosphino)methyl]pyrrolidine (2.50 g, 9.28 mmol) in dichloromethane (27 ml). The resulting solution was stirred at 30° C. overnight. The reaction mixture was poured into water/dichloromethane (100 ml/100 ml). The crude residue was extracted with dichloromethane (100 ml), the organic phase was washed with water (100 ml), followed by brine (100 ml) and then dried over sodium sulfate and concentrated under reduced pressure. Purification by column chromatography ([5:95], methanol:dichloromethane) afforded the title compound as a yellow viscous oil (1.57 g) 47% yield.

$^1$H NMR (500 MHz, cdcl3) δ=7.50-7.39 (m, 4H, CH—Ar), 7.37-7.28 (m, 6H, CH—Ar), 3.66 (s, 3H, CH$_3$-9), 3.19-3.03 (m, 2H, CH$_2$-5,6), 2.54 (dt, J=3.3, 13.3, 1H, CH$_2$-4), 2.49-2.29 (m, 4H, CH-2, CH$_2$-6,7), 2.15-2.06 (m, 1H, CH$_2$-5), 2.06-1.91 (m, 21-1, CH$_2$-1,3), 1.83-1.53 (m, 3H, CH$_2$-3,4).

$^{13}$C NMR (126 MHz, cdcl3) δ=172.85 (s, C-8), 139.28 (d, J=12.1, Ar), 138.47 (d, J=13.3, Ar), 132.95 (d, J=19.3, Ar), 132.57 (d, J=18.7, Ar), 128.68 (s, Ar), 128.45 (s, Ar), 128.40 (s, Ar), 128.35 (s, Ar), 128.33 (s, Ar), 128.28 (s, Ar), 62.08 (d, J=19.3, C-2), 53.44 (d, J=0.8, C-5), 51.50 (s, C-9), 49.09 (s, C-6), 33.62 (d, J=13.3, C-1), 33.48 (s, C-7), 31.67 (d, J=7.8, C-3), 22.21 (d, J=0.6, C-4).

IR (diamond, V$_{MAX}$, cm$^{-1}$) 2961, 2802 (CH$_3$O st), 1735 (C=O st), 1433 (H—C—H st as), 1175 (C—O st as).

Acc. Mass (FAB): C$_{21}$H$_{27}$NO$_2$P

Calculated: 356.1774

Found: 356.1778 error [ppm]: −1.28

Synthesis Example 5b

3-{(2S)-2-[(diphenylphosphing)methyl]pyrrolidin-1-yl}propanoic acid (14)

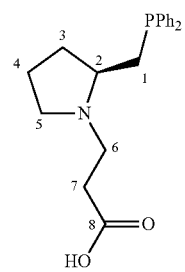

14

A 1 N solution of sodium hydroxide (34.3 ml) was added to methyl 3-{(2S)-2-[(diphenylphosphino)methyl]pyrrolidin-1-yl}propanoate (13) (0.50 g, 1.41 mmol, 0.062 M) in methanol (22.85 ml). After stirring for 20 h at room temperature the reaction mixture was neutralize with 3.5 ml of 32% hydrochloric acid. The resulting solution was lyophilised. Methanol was added to dissolve the crude product and insoluble salts was removed by filtration. The resulting solution was dried over magnesium sulfate; the filtrate was evaporated under reduced pressure. Purification by column chromatography ([5:95], methanol:dichloromethane) afforded the title compound as yellow viscous oil (0.57 g) 100% yield.

$^1$H NMR (500 MHz, CDCl$_3$) δ=8.46-7.74 (m, 2H), 7.40 (m, 10H, CH—Ar), 3.70-3-80 (m, 1H, CH$_2$-5), 3.61-3.49 (m, 1H, CH$_2$-7), 3.06-2.72 (m, 6H, CH-2, CH$_2$-1,6,7,5), 2.64 (t, J=12.1, 1H, CH$_2$-1), 2.24-1.82 (m, 4H, CH$_2$-3,4).

$^{13}$C NMR (126 MHz, CDCl$_3$) δ=173.21 (s, C-8), 136.82 (d, J=11.3, Ar), 136.13 (d, J=12.7, Ar), 133.01 (d, J=20.2, Ar), 132.50 (d, J=19.2, Ar), 129.62 (s, Ar), 129.09 (s, Ar), 128.94 (d, J=7.3, Ar), 128.68 (d, J=6.9, Ar), 66.94 (d, J=23.2, C-2), 52.82 (s, C-5), 49.35 (s, C-7), 31.12 (s, C-6), 30.48 (d, J=7.4, C-3), 29.60 (d, J=16.2, C-1), 21.74 (s, C-4).

$^{31}$P NMR (162 MHz, CDCl$_3$) δ=−20.61 (sy, 30.40 (s, P=O, 5%).

Acc. Mass (FAB): C$_{20}$H$_{25}$NO$_2$P

Calculated: 342.1617

Found: 342.1608 error [ppm]: 2.86

IR (diamond, v$_{max}$, cm$^{-1}$) 2956.45, 2547.43 (HO st), 1720.49 (C=O st), 1432.90 (H—C—H st as)

Synthesis Example 5c

Compound 12

3-{(2S)-2-[(diphenylphosphino)methyl]pyrrolidin-1-yl}propanoic acid (14)

(0.50 g, 1.46 mmol), triflic amine (0.2184 g, 1.46 mmol) and HOBt*H$_2$O (0.2242 g, 1.46 mmol) were dissolved in dichloromethane (3.85 ml) and cooled to 0° C. EDC (0.2331 g, 1.50 mmol) was added and mixture was stirred for 15 min at 0° C. and at room temperature overnight. The precipitate was filtered off and solvent was evaporated. The residue was dissolved in 20 ml of dichloromethane and washed with 1M citric acid (20 ml), saturated NaHCO$_3$ (20 ml), brine (20 ml) and dried over anhydrous magnesium sulfate; concentrated under reduced pressure. Purification by column chromatography ([5:95], methanol:dichloromethane) afforded the title compound as white solid (0.34 g) 49% yield.

$^1$H NMR (500 MHz, DMSO) δ=7.55-7.32 (m, 10H, CH—Ar), 3.75-3.45 (m, 2H, CH$_2$-5,6), 3.22 (s, 1H, CH-2), 3.11-2.89 (m, 3H, CH$_2$-1,5,6), 2.55-2.45 (m, 2H, CH$_2$-7), 2.28 (t, J=12.1, 1H, CH$_2$-1), 2.07 (m, 1H, CH$_2$-3), 1.94-1.77 (m, 2H, CH$_2$-4), 1.67 (m, 1H, CH$_2$-3).

13C NMR (126 MHz, DMSO) δ=174.33 (s, C-8), 137.32 (d, J=12.2, C—Ar), 136.24 (d, J=13.2, C—Ar), 132.67 (d, J=19.9, C—Ar), 132.40 (d, J=19.6, C—Ar), 129.23 (d, J=33.7, C—Ar), 128.79 (d, J=7.1, C—Ar), 128.64 (d, J=7.0, C—Ar), 124.10 (s, CF), 121.52 (s, CF), 118.93 (s, CF), 116.35 (s, CF), 66.12 (d, J=23.5, C-2), 52.78 (s, C-5), 49.59 (s, C-6), 34.32 (s, C-7), 30.10 (s, C-3), 28.92 (d, J=13.0, C-1), 21.35 (s, C-4).

$^{31}$P NMR (162 MHz, DMSO) δ=−21.76 (s).

$^{19}$F NMR (376 MHz, DMSO) δ=−77.71 (s).

Acc. Mass (FAB): C$_{21}$H$_{24}$F$_3$N$_2$NaO$_3$PS

Calculated: 495.1090

Found: 495.1117 error [ppm]: −5.50

IR (diamond, v$_{max}$, cm$^{-1}$) 3052.64, 2967.30 (NH st), 2191.80 (Ar comb), 1598.44 (C=O st amide), 1431.16 (H—C—H st as), 1175.92 (S—O st as), 1123.44 (S—O st sy)

Synthesis Example 5d

Compound 15

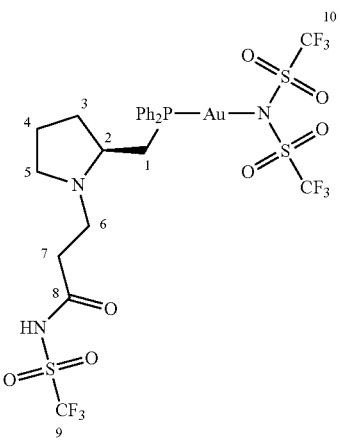

The solution gold phosphine chloride (65.2 mg, 0.092 mmol) in dichloromethane (0.31 ml) was added to premixed (5 min) solution of bistriflic amide (26 mg, 0.092 mmol) and silver carbonate (25.5 mg, 0.092 mmol) in dry dichloromethane (2 ml) under inert atmosphere. The resulting mixture was stirred in the dark room for 2 h. The mixture was filtered by the celite. The evaporation of the solvent afforded the title compound 15 as an off white solid with (70.5 mg) 80% yield.

$^1$H NMR (500 MHz, CDCl$_3$) δ=8.17-6.96 (m, 10H, CH—Ar), 3.51 (m, 9H, CH-2, CH$_2$-1,5,6,7), 1.96 (m, 3H, CH$_2$-3,4), 1.33 (m, 1H, CH$_2$-3).

$^{13}$C NMR (126 MHz, CDCl$_3$) δ=174.76 (s, C-8), 134.90 (d, J=14.0, C—Ar), 133.82 (s, C—Ar), 132.16 (s, C—Ar), 131.71 (d, J=12.2, C—Ar), 129.98 (s, C—Ar), 129.81-129.57 (m, C—Ar), 129.42 (d, J=11.7, C—Ar), 123.43 (s, CF), 120.87 (s, CF), 118.32 (s, CF), 115.83-115.70 (m, CF), 64.74-63.97 (m, C-2), 52.82 (s, C-5), 44.93 (s, C-6), 29.47, 29.14 (s, C-1,3,7), 20.80 (s, C-4).

$^{31}$P NMR (162 MHz, CDCl$_3$) δ=26.78 (s).

$^{19}$F NMR (376 MHz, CDCl$_3$) δ=−76.56 (s), −78.68 (s).

IR (diamond, v$_{MAX}$, cm$^{-1}$) 2177.92 (Ar comb), 1669.63 (C=O st amide), 1438.66 (H—C—H st as), 1178.46 (S—O st as), 1127.69 (S—O st sy)

Synthesis Example 5e

Compound 16

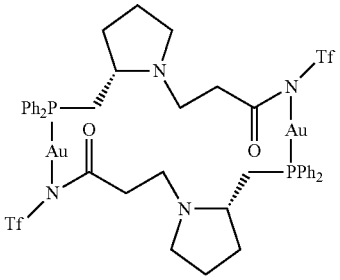

The 3-{(2S)-2-[(diphenylphosphino)methyl]pyrrolidin-1-yl}-N-[(trifluoromethyl) sulfonyl]propanamide 12 (100 mg, 0.212 mmol) was placed in dry round bottom flask under inert atmosphere and dissolved in dry dichloromethane (2.1 ml). The dimethyl sulfide gold chloride was added in one portion and mixture was stirring 15 min. The silver carbonate (58.4 mg, 0.212 mmol) was added in one portion and resulting mixture was stirred overnight. The reaction was filtered by celite. The evaporation of the solvent afforded the title compound 16 as a yellow solid (139.2 mg).

$^1$H NMR (500 MHz, CDCl$_3$) δ=7.91-7.37 (m, 10H), 3.36-1.23 (m, 13H).

$^{13}$C NMR (100 MHz, CDCl$_3$) δ=176.87-176.59 (m, C=O), 133.59 (s, Ar), 132.95 (s, Ar), 132.20 (s, Ar), 129.54 (t, J=28.3, Ar), 125.52-125.31 (m, CF), 122.09 (s, CF), 119.00-118.66 (m, CF), 115.83-115.49 (m, CF), 61.75 (s), 53.39 (s), 50.04 (s), 37.88-36.86 (m), 33.67-32.73 (m), 31.90 (s), 22.79 (s).

$^{31}$P NMR (162 MHz, CDCl$_3$) δ=21.60 (d, J=149.3).

IR (diamond, ν$_{MAX}$, cm$^{-1}$) 2961.79 (NH st), 2167.92 (Ar comb), 1683.13 (C=O st amide), 1436.97 (H—C—H st as), 1177.16 (S—O st as), 1121.41 (S—O st sy).

Acc. Mass (FAB): C$_{42}$H$_{47}$ AU$_2$F$_6$N$_4$O$_6$P$_2$S$_2$ Found: 1337.1704 m/z Calculated: 1337.1704 m/z.

CATALYTIC EXAMPLES

Catalytic Example 1

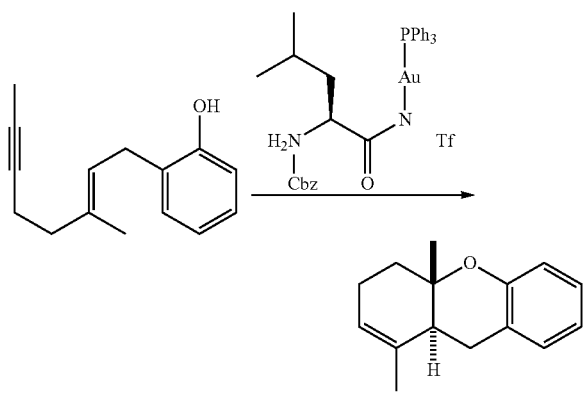

The (E)-2-β-methyloct-2-en-6-yn-1-yl)phenol (50 mg, 0.24 mmol) was placed in dried round bottom flask under nitrogen. CH$_2$Cl$_2$ (0.48 ml, 0.5 M) was added and the mixture was stirred for 2 minutes. The catalyst 9a was added and the reaction mixture was stirred for 5 days at room temperature.

The solvent was concentrated under reduced pressure. Purification by column chromatography ([99:1], cyclohexane:ethyl acetate) afforded the title compound as light yellow oil (yield: 78%).

Equivalent reactions were performed using other catalysts according to the invention. These data are summarised in the following table:

| Cat. | Mol % | Solvent | Time | T [C. °] | Yield [%] |
|------|-------|---------|------|----------|-----------|
| 7    | 5     | CH$_2$Cl$_2$ | 5 Days | RT | 46 |
| 9a   | 27    | CH$_2$Cl$_2$ | 16 h   | RT | 76 |
| 9a   | 5     | CH$_2$Cl$_2$$^a$ | 5 Days | RT | 78 |
| 9a   | 5     | Benzene | 5 Days | RT | 63 |

$^a$laboratory reagent grate

Catalytic Example 2

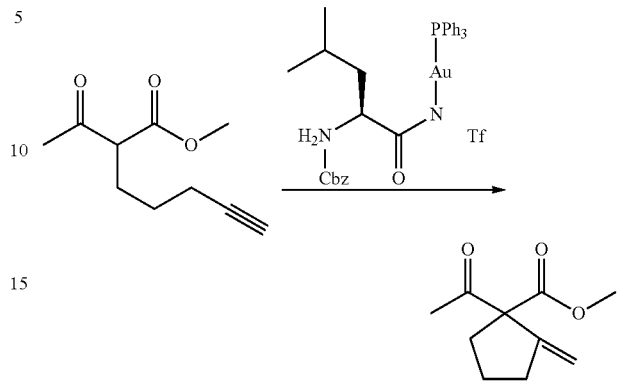

Methyl 2-acetylhept-6-ynoate (50 mg, 0.27 mmol) was placed in dried round bottom flask under nitrogen. 1,2-dichloroethane (0.69 ml, 0.4 M) was added and the mixture was stirred for 2 minutes. The catalyst 9a (11.7 mg, 0.014 mmol, 0.05 mol %) was added and the reaction mixture was stirred for 5 days at 50° C. The reaction was concentrated under reduced pressure. Purification by column chromatography ([99:1], cyclohexane:ethyl acetate) afforded the title compound as colorless yellow oil (yield: 81%).

Equivalent reactions were performed using other catalysts according to the invention. These data are summarised in the following table:

| Cat. | Mol % | Solvent | Time | T [C. °] | Yield [%] | [α]$_D$ |
|------|-------|---------|------|----------|-----------|---------|
| 9a   | 5     | (CH$_2$)$_2$Cl$_2$ | 5 Days | 50 | 81 |      |
| 15   | 1 + 1$^a$ | CH$_2$Cl$_2$ | 2 Days | RT | 73 | -3.2 |
| 15   | 2     | CH$_2$Cl$_2$ | 2 Days | RT | 65 | -3.0 |
| 15   | 1     | (CH$_2$)$_2$Cl$_2$ | 24 h | 50 | 58 | -1.2 |
| 16   | 5     | CH$_2$Cl$_2$ | 5 Days | RT | 33 | 2.4 |
| 16   | 5     | (CH$_2$)$_2$Cl$_2$ | 14 h | 70 | 75 | 3.2 |

Catalytic Example 3

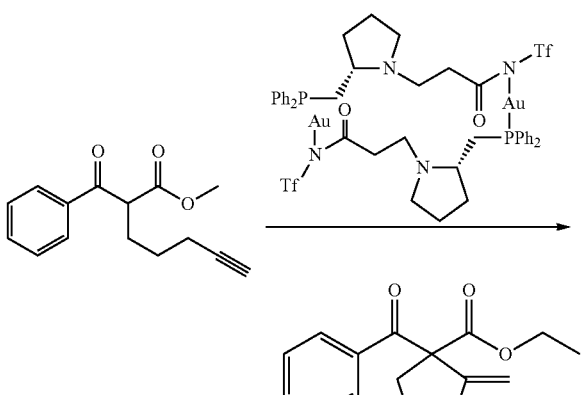

This reaction was reported for Au(I) by Toste, D et. al. *J. Am. Chem. Soc.* 2004, 126, 4526.

Ethyl 2-benzoylhept-6-ynoate (71 mg, 0.27 mmol) was placed in a round bottom flask under nitrogen. 1,2-Dichloroethane (0.69 ml, 0.4 M) was added and the mixture was stirred for 2 minutes. The catalyst 13 was added and the reaction mixture was stirred for 5 days at 70° C.

The solvent was concentrated under reduced pressure. Purification by column chromatography ([95:5], hexanes: ethyl acetate or diethyl ether) afforded the title compound as colorless oil (65 mg, 91%). $[\alpha]_D$=8.4.

The invention claimed is:

1. A catalytic process using a catalyst comprising an enantiomerically enriched compound of formula (II):

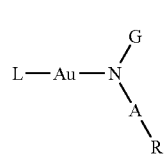

wherein L denotes a phosphine, thioether, amine or N-heterocyclic carbene ligand;
A denotes $SO_2$, C(=O), or $P(O)(R^1)_2$ each $R^1$ independently denotes alkyl, cycloalkyl; or
optionally substituted aryl;
R denotes hydrogen, alkyl, or haloalkyl; or optionally substituted (hetero) aryl; and
G denotes a group deriving from an α- or β-amino acid,
wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);
the process comprising a reaction comprising nucleophilic attack on a π-system by a nucleophile, wherein the nucleophile comprises an alcohol, water, an amine, a thiol, a halogen or mixtures thereof.

2. The process of claim 1, wherein the π-system comprises a carbon-carbon double bond.

3. The process of claim 1, wherein the π-system comprises a carbon-carbon triple bond.

4. The process of claim 1, wherein the process is stereoselective.

5. A catalytic process using a catalyst comprising an enantiomerically enriched compound of formula (II):

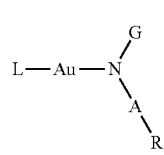

wherein L denotes a phosphine, thioether, amine or N-heterocyclic carbene ligand;
A denotes $SO_2$, C(=O), or $P(O)(R^1)_2$ each $R^1$ independently denotes alkyl or cycloalkyl;
or optionally substituted aryl;
R denotes hydrogen, alkyl, or haloalkyl; or optionally substituted (hetero) aryl; and
G denotes a group deriving from an α- or β-amino acid,
wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);
the process comprising an addition reaction comprising the hydration of a π-system.

6. The process of claim 5, wherein the π-system comprises a carbon-carbon double bond.

7. The process of claim 5, wherein the π-system comprises a carbon-carbon triple bond.

8. The process of claim 5, wherein the process is stereoselective.

9. A catalytic process using a catalyst comprising an enantiomerically enriched compound of formula (II):

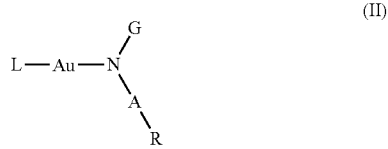

wherein L denotes a phosphine, thioether, amine or N-heterocyclic carbene ligand;
A denotes $SO_2$, C(=O), or $P(O)(R^1)_2$ each $R^1$ independently denotes alkyl or cycloalkyl;
or optionally substituted aryl;
R denotes hydrogen, alkyl, or haloalkyl; or optionally substituted (hetero)aryl; and
G denotes a group deriving from an α- or β-amino acid,
wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);
the process comprising a reaction comprising cyclization between a π-system and an internal nucleophile, thereby forming a ring compound.

10. The process of claim 9 wherein in the ring comprises a 3-7 membered ring bearing one or more heteroatoms.

11. The process of claim 9 wherein the reaction is a cyclopropanation.

12. The process of claim 9, wherein the process is stereoselective.

13. A catalytic process using a catalyst comprising an enantiomerically enriched compound of formula (II):

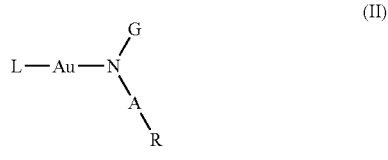

wherein L denotes a phosphine, thioether, amine or N-heterocyclic carbene ligand;
A denotes $SO_2$, C(=O), or $P(O)(R^1)_2$ each $R^1$ independently denotes alkyl or cycloalkyl;
or optionally substituted aryl;
R denotes hydrogen, alkyl, or haloalkyl; or optionally substituted (hetero)aryl; and
G denotes a group deriving from an α- or β-amino acid,
wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);

and wherein the process comprises a Rautenstrauch rearrangement reaction.

14. The process of claim 13, wherein the process is stereoselective.

15. A catalytic process using a catalyst comprising an enantiomerically enriched compound of formula (II):

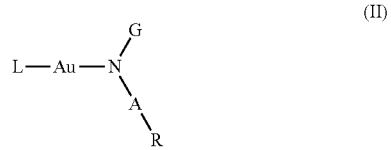

(II)

wherein L denotes a phosphine, thioether, amine or N-heterocyclic carbene ligand;

A denotes $SO_2$, $C(=O)$, or $P(O)(R^1)_2$ each $R^1$ independently denotes alkyl or cycloalkyl;

or optionally substituted aryl;

R denotes hydrogen, alkyl, or haloalkyl; or optionally substituted (hetero)aryl; and G denotes a group deriving from an α- or β-amino acid, wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);

and wherein the process comprises a Schmidt reaction.

16. The process of claim 15, wherein the process is stereoselective.

17. A catalytic process using a catalyst comprising an enantiomerically enriched compound of formula (II):

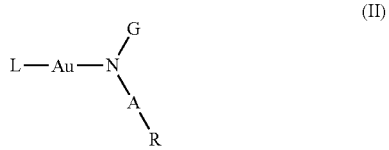

(II)

wherein L denotes a phosphine, thioether, amine or N-heterocyclic carbene ligand;

A denotes $SO_2$, $C(=O)$, or $P(O)(R^1)_2$ each $R^1$ independently denotes alkyl or cycloalkyl;

or optionally substituted aryl;

R denotes hydrogen, alkyl, or haloalkyl; or optionally substituted (hetero) aryl; and G denotes a group deriving from an α- or β-amino acid, wherein optionally together G and L may combine to form a macrocycle containing the Au metal, or alternatively L may derive from a G sub stituent in an identical compound of formula (II), such that a macrocycle containing two Au atoms is formed, with the L substituent on each Au metal atom deriving from the G substituent on the corresponding compound of formula (II);

and wherein the process comprises a Claisen rearrangement reaction.

18. The process of claim 17, wherein the process is stereoselective.

* * * * *